(12) United States Patent
Kurosaki et al.

(10) Patent No.: US 10,869,995 B2
(45) Date of Patent: Dec. 22, 2020

(54) BALLOON WRAPPING APPARATUS AND BALLOON WRAPPING METHOD

(71) Applicant: TERUMO KABUSHIKI KAISHA, Tokyo (JP)

(72) Inventors: Yasuo Kurosaki, Kanagawa (JP); Hiroshi Goto, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 135 days.

(21) Appl. No.: 15/928,542

(22) Filed: Mar. 22, 2018

(65) Prior Publication Data

US 2018/0207410 A1 Jul. 26, 2018

Related U.S. Application Data

(63) Continuation of application No. PCT/JP2016/078035, filed on Sep. 23, 2016.

(30) Foreign Application Priority Data

Sep. 25, 2015 (JP) ................................ 2015-188027

(51) Int. Cl.
*A61M 25/10* (2013.01)
*B29C 51/10* (2006.01)
(Continued)

(52) U.S. Cl.
CPC ......... *A61M 25/1038* (2013.01); *B29C 51/10* (2013.01); *B29C 53/08* (2013.01);
(Continued)

(58) Field of Classification Search
CPC ........ A61M 25/1038; A61M 2025/105; B29C 70/682; B29C 53/825; B29C 53/566; B29C 53/08; B29C 51/10; B29L 2031/7543
See application file for complete search history.

(56) References Cited

U.S. PATENT DOCUMENTS

| | | |
|---|---|---|
| 5,350,361 A | 9/1994 | Tsukashima et al. |
| 7,762,804 B1 | 7/2010 | Stupecky |
| (Continued) | | |

FOREIGN PATENT DOCUMENTS

| | | |
|---|---|---|
| CN | 1680771 A | 10/2005 |
| CN | 103167846 A | 6/2013 |
| (Continued) | | |

OTHER PUBLICATIONS

The extended European Search Report dated Mar. 14, 2019, by the European Patent Office in corresponding European Patent Application No. 16848665.2-1132. (8 pages).
(Continued)

*Primary Examiner* — Michael N Orlando
*Assistant Examiner* — Christopher W Raimund
(74) *Attorney, Agent, or Firm* — Buchanan Ingersoll & Rooney PC

(57) ABSTRACT

A balloon wrapping apparatus and a balloon wrapping method are disclosed by which a balloon can be accurately positioned in relation to a pleating section and to a folding section. The balloon wrapping apparatus for wrapping a balloon of a balloon catheter provided with the balloon at a distal portion of an elongated shaft includes: a pleating section having a plurality of blades aligned with space parts therebetween in a circumferential direction, and forms the balloon with wing shapes projecting in radial directions by clamping the balloon in the space parts by moving rotationally the blades; and a folding section having a plurality of blades aligned in a circumferential direction, and that folds the wing shapes formed in the balloon in the circumferential direction by moving rotationally the blades; and a support base that supports a part of the shaft which part is on a proximal side of the balloon.

20 Claims, 15 Drawing Sheets

(51) Int. Cl.
    *B29C 53/08*     (2006.01)
    *B29C 53/56*     (2006.01)
    *B29C 53/82*     (2006.01)
    *B29C 70/68*     (2006.01)
    *B29L 31/00*     (2006.01)

(52) U.S. Cl.
    CPC .......... *B29C 53/566* (2013.01); *B29C 53/825* (2013.01); *B29C 70/682* (2013.01); *A61M 2025/105* (2013.01); *B29L 2031/7543* (2013.01)

(56) References Cited

U.S. PATENT DOCUMENTS

| | | |
|---|---|---|
| 2001/0037140 A1 | 11/2001 | Gaudoin et al. |
| 2002/0163104 A1* | 11/2002 | Motsenbocker .. A61M 25/1002 264/320 |
| 2005/0177130 A1 | 8/2005 | Konstantino et al. |
| 2005/0235514 A1* | 10/2005 | Otsubo ................ G01B 5/0009 33/712 |
| 2005/0277877 A1 | 12/2005 | Motsenbocker et al. |
| 2012/0042501 A1* | 2/2012 | Wang ..................... B29D 23/00 29/505 |
| 2013/0303982 A1 | 11/2013 | Morero et al. |
| 2014/0319750 A1* | 10/2014 | Yanes ............... A61M 25/1038 269/86 |
| 2015/0174384 A1 | 6/2015 | Chappa et al. |

FOREIGN PATENT DOCUMENTS

| | | |
|---|---|---|
| CN | 204379958 U | 6/2015 |
| JP | 2002-512862 A | 5/2002 |
| JP | 2004-525704 A | 8/2004 |
| JP | 2006-271678 A | 10/2006 |
| JP | 2007-521878 A | 8/2007 |
| JP | 2013-056071 A | 3/2013 |
| WO | WO 2013/173186 A1 | 11/2013 |
| WO | WO-2014076776 A1 * | 5/2014 ........ A61M 25/1038 |

OTHER PUBLICATIONS

International Search Report (PCT/ISA/210) dated Dec. 20, 2016, by the Japanese Patent Office as the International Searching Authority for International Application No. PCT/JP2016/078035.

Written Opinion (PCT/ISA/237) dated Dec. 20, 2016, by the Japanese Patent Office as the International Searching Authority for International Application No. PCT/JP2016/078035.

English translation of International Search Report issued in International Patent Application No. PCT/JP2016/078035, 2 pages (dated Dec. 20, 2016).

English translation of Written Opinion issued in International Patent Application No. PCT/JP2016/078035, 6 pages (dated Dec. 20, 2016).

The First Office Action issued by The State Intellectual Property Office of People's Republic of China in corresponding Chinese Patent Application No. 201680055319.1 dated Mar. 27, 2020 (15 pages including partial English translation).

* cited by examiner

Table 1

| Conditions | Comparative Example 1 | Comparative Example 2 | Comparative Example 3 | Comparative Example 4 | Comparative Example 5 |
|---|---|---|---|---|---|
| Diameter/length of balloon | 2.0 mm/40 mm | 4.0 mm/200 mm | 3.0 mm/200 mm | 2.0 mm/200 mm | 6.0 mm/200 mm |
| Material of balloon | Nylon | Nylon | Nylon | Nylon | Nylon |
| Surface condition of balloon catheter | Smooth, non-porous | Smooth, non-porous | Smooth, non-porous | Smooth, non-porous | Smooth, non-porous |
| Amount of paclitaxel | 3.2 µg/mm$^2$ | 3.6 µg/mm$^2$ | 3.6 µg/mm$^2$ | 3.2 µg/mm$^2$ | 3.2 µg/mm$^2$ |
| Diameter/length of core metal member | 0.39 mm/700 mm | 0.38 mm/500 mm | 0.38 mm/500 mm | 0.38 mm/700 mm | 0.48 mm/700 mm |
| Shape of core metal member | Wire-like | Wire-like | Wire-like | Wire-like | Wire-like |
| Material of core metal member | SUS | SUS | SUS | SUS | SUS |
| Material of holding portion | Silicone rubber | Silicone rubber | Silicone rubber | Silicone rubber | Silicone rubber |
| Shape/function of distal support of pleating section | Insertion into distal support | Insertion into distal support | Insertion into distal support | Insertion into distal support | Insertion into distal support |
| Number of blades in pleating section | Three | Three | Three | Three | Four |
| Characteristics of films | Difficult to electrostatically charge, smooth | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm | Teflon/0.001 mm |
| Control of pulling by collet chuck | - | - | - | - | - |
| Shape/function of distal support of folding section | Insertion into central portion of distal support | Insertion into central portion of distal support | Insertion into central portion of distal support | Insertion into central portion of distal support | Insertion into central portion of distal support |
| Number of blades in folding section | Ten | Ten | Ten | Ten | Ten |
| Control of pulling by collet chuck | - | - | - | - | - |
| Timing of start of rotation | Point of time when films contacted wings | - | - | Point of time when films contacted wings | - |
| Rotation of balloon catheter as viewed from proximal side | Counterclockwise | - | - | Counterclockwise | - |

FIG. 17

Table 2

| Conditions | Example 1 | Example 2 | Example 3 | Example 4 |
|---|---|---|---|---|
| Diameter/length of balloon | 6.0 mm/200 mm | 4.0 mm/200 mm | 4.0 mm/200 mm | 4.0 mm/200 mm |
| Material of balloon | Nylon | Nylon | Nylon | Nylon |
| Surface condition of balloon catheter | Smooth, non-porous | Smooth, non-porous | Smooth, non-porous | Smooth, non-porous |
| Amount of paclitaxel | 3.2 µg/mm$^2$ | 3.2 µg/mm$^2$ | 3.2 µg/mm$^2$ | 3.2 µg/mm$^2$ |
| Diameter/length of core metal member | 0.48 mm/700 mm | 0.48 mm/700 mm | 0.48 mm/700 mm | 0.48 mm/700 mm |
| Shape of core metal member | Wire-like | Hollow | Hollow | Hollow |
| Material of core metal member | SUS | SUS | SUS | SUS |
| Material of holding portion | Silicone rubber | Silicone rubber | Silicone rubber | Silicone rubber |
| Shape/function of distal support of pleating section | Clamping in collet chuck | Clamping in collet chuck | Clamping in collet chuck | Clamping in collet chuck |
| Number of blades in pleating section | Four | Four | Four | Four |
| Characteristics of films | Difficult to electrostatically charge, smooth | Difficult to electrostatically charge, smooth | Difficult to electrostatically charge, smooth | Difficult to electrostatically charge, smooth |
| Film (material/thickness) | Teflon/0.001 mm | Teflon/0.001 mm | Teflon/0.001 mm | Teflon/0.001 mm |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |
| Shape/function of distal support of folding section | Clamping in collet chuck | Clamping in collet chuck | Clamping in collet chuck | Clamping in collet chuck |
| Number of blades in folding section | Eight | Twelve | Twelve | Twelve |
| Control of pulling by collet chuck | Distal support is fixed at prescribed position and then support base is pulled backward by 5 mm | Distal support is pulled further forward by 5 mm from prescribed position and fixed | Distal support is fixed at prescribed position and then support base is pulled backward with force of 5 N | Distal support is pulled further from prescribed position with force of 1 N and fixed |
| Timing of start of rotation | Point of time when films contacted wings | Point of time when films contacted wings | Point of time when films contacted wings | Point of time when films contacted wings |
| Rotation of balloon catheter as viewed from proximal side | Counterclockwise | Counterclockwise | Counterclockwise | Counterclockwise |

FIG. 18

Table 3

| Conditions | Comparative Example 6 | Comparative Example 7 | Comparative Example 8 | Comparative Example 9 |
|---|---|---|---|---|
| Diameter/length of balloon | 3.0 mm/20 mm | 4.0 mm/200 mm | 3.0 mm/200 mm | 2.0 mm/200 mm |
| Material of balloon | Nylon elastomer | Nylon | Nylon | Nylon |
| Surface condition of balloon catheter | Smooth, non-porous | Smooth, non-porous | Smooth, non-porous | Smooth, non-porous |
| Amount of paclitaxel | 3.2 µg/mm$^2$ | 3.6 µg/mm$^2$ | 3.6 µg/mm$^2$ | 3.2 µg/mm$^2$ |
| Diameter/length of core metal member | 0.38 mm/500 mm | 0.38 mm/500 mm | 0.38 mm/500 mm | 0.38 mm/700 mm |
| Shape of core metal member | Wire-like | Wire-like | Wire-like | Wire-like |
| Material of core metal member | SUS | SUS | SUS | SUS |
| Material of holding portion | Silicone rubber | Silicone rubber | Silicone rubber | Silicone rubber |
| Shape/function of distal support of pleating section | Insertion into distal support | Insertion into distal support | Insertion into distal support | Clamping in collet chuck |
| Number of blades in pleating section | Three | Three | Three | Four |
| Characteristics of films | Difficult to electrostatically charge, smooth | - | - | Difficult to electrostatically charge, smooth |
| Film (material/thickness) | Teflon/0.001 mm | None | None | Teflon/0.001 mm |
| Control of pulling by collet chuck | - | - | - | - |
| Shape/function of distal support of folding section | Insertion into distal support | Insertion into distal support | Insertion into distal support | Insertion into distal support |
| Number of blades in folding section | Twelve | Ten | Ten | Ten |
| Control of pulling by collet chuck | - | - | - | - |
| Timing of start of rotation | Point of time when films contacted wings | - | - | - |
| Rotation of balloon catheter as viewed from proximal side | Counterclockwise | - | - | - |

FIG. 19

Table 4

| Examples | Presence /absence of films | Size (diameter/length) of balloon | Amount of paclitaxel per unit area [μg/mm²] | | Retention rate of paclitaxel (%) |
| --- | --- | --- | --- | --- | --- |
| | | | After coating | After folding | |
| Comparative Example 1 | Present | 2.0 mm/40 mm | 3.2 | 2.8 | 88 |
| Comparative Example 2 | Present | 4.0 mm/200 mm | 3.6 | 3.5 | 97 |
| Comparative Example 3 | Present | 3.0 mm/200 mm | 3.6 | 3.3 | 92 |
| Comparative Example 4 | Present | 2.0 mm/200 mm | 3.2 | 3.1 | 96 |
| Comparative Example 5 | Present | 6.0 mm/200 mm | 3.2 | 3.1 | 97 |
| Comparative Example 7 | Absent | 4.0 mm/200 mm | 3.6 | 2.8 | 78 |
| Comparative Example 8 | Absent | 3.0 mm/200 mm | 3.6 | 2.6 | 72 |

FIG. 20

Table 5

| Examples | Rotation of balloon during folding | Number of drug-coated balloons in which back folding was generated [(Number of drug-coated balloons in which back folding was generated)/(Total number of drug-coated balloons subjected to folding)] | Generation rate of back folding [%] |
|---|---|---|---|
| Comparative Example 4 | Performed | 1/142 | 0.7 |
| Comparative Example 9 | Not performed | 22/46 | 48 |

FIG. 21

BALLOON WRAPPING APPARATUS AND BALLOON WRAPPING METHOD

CROSS-REFERENCES TO RELATED APPLICATIONS

This application is a continuation of International Application No. PCT/JP2016/078035 filed on Sep. 23, 2016, which claims priority to Japanese Application No. 2015-188027 filed on Sep. 25, 2015, the entire contents of both of which are incorporated herein by reference.

TECHNICAL FIELD

The present disclosure relates to a balloon wrapping apparatus and a balloon wrapping method for wrapping a balloon of a balloon catheter.

BACKGROUND ART

Treatment of a lesion of a blood vessel by use of a catheter has been widely practiced because of little surgical invasiveness. For example, in percutaneous coronary angioplasty (Percutaneous Transluminal Coronary Angioplasty), a balloon catheter can be used for improving blood flow by pushing open a lesion part of a coronary artery. In general, a balloon catheter includes an elongated hollow shaft, a balloon provided on the distal side of the shaft, and a hub provided on the proximal side of the shaft. The balloon catheter may be provided with a drug eluting balloon having a surface coated with a drug.

The balloon of a balloon catheter is required to be as small as possible in diameter when deflated, for good passing properties in a blood vessel. The balloon is formed in a small diameter form by being wrapped at the time of manufacturing the catheter. The wrapping of the balloon is conducted by a pleating step of bending the balloon to form a plurality of wing shapes, for example, three or four wing shapes in the circumferential direction, and a folding step of folding the thus formed wing shapes toward one side in the circumferential direction.

As a conventional balloon wrapping apparatus, there may be mentioned, for example, the one described in JP-T-2004-525704. The balloon wrapping apparatus has a pleating section for performing pleating, and a folding section for performing folding. In addition, the balloon wrapping apparatus has a support base which supports the shaft of the balloon catheter and which is slidable such that the balloon can be inserted into each head.

The pleating section has a plurality of blades in the circumferential direction for shaping the balloon to have the wings. Between the plurality of blades, a space part extending along an insertion direction of the balloon is formed. In addition, the blades can be moved rotationally in such a manner as to change the shape of the space part. The balloon is inserted into the space part between the blades, and the balloon is narrowed by the blades moved rotationally, whereby wing shapes are formed.

The folding section has a plurality of blades movable rotationally such that the wing shapes formed in the balloon can be folded in the manner of being laid flat along the circumferential direction. The balloon is inserted into a region surrounded by the plurality of blades, and the blades are moved rotationally such as to close the region between the blades, whereby the wing shapes formed in the balloon are folded along the circumferential direction.

When wrapping the balloon, the balloon catheter is placed on the support base, and the support base is slid toward the pleating section, whereby the balloon is advanced into the pleating section, and pleating is conducted. When the balloon is drawn out of the pleating section, the balloon is subsequently advanced into the folding section, and folding is conducted.

SUMMARY OF INVENTION

For improving passing properties of the balloon, the wing shapes should be formed into an accurate shape on the basis of a predetermined interval along the circumferential direction in wrapping of the balloon. For this purpose, the balloon should be positioned accurately at a center position of the pleating section. If the position of the balloon is deviated from the center position of the pleating section, the wing shapes formed in pleating may not become uniform. In addition, if the position of the balloon is deviated from the center position of the folding section, the wing shapes may be crushed at irregular parts, or back folding in which the wing shape is folded in the reverse direction in the circumferential direction may occur.

When the catheter is placed on the support base and the balloon is inserted into the pleating section, a portion near the distal end of the catheter having the balloon is not supported by the support base, and, therefore, the catheter is bent downward due to balloon's own weight. Accordingly, it can be difficult to accurately position the balloon at the center position of the pleating section or the folding section.

In accordance with an exemplary embodiment, a balloon wrapping apparatus and a balloon wrapping method are disclosed by which a balloon can be accurately positioned in relation to a pleating section and to a folding section.

In accordance with an exemplary embodiment, a balloon wrapping apparatus is disclosed for wrapping a balloon of a balloon catheter provided with the balloon at a distal portion of an elongated shaft, the balloon wrapping apparatus including: a pleating section that has a plurality of wing forming members aligned with space parts therebetween in a circumferential direction, and that forms the balloon with wing shapes projecting in radial directions by clamping by the wing forming members the balloon caused to enter into the space parts by moving rotationally the wing forming members; a folding section that has a plurality of folding members aligned in a circumferential direction, and that folds the wing shapes formed in the balloon in a circumferential direction by moving rotationally the folding members; a support base that supports a part of the shaft which part is on a proximal side of the balloon, and that makes the distal portion of the shaft positionable in relation to the pleating section and the folding section; and a grasping section capable of grasping a part of the balloon catheter which part is on a distal side of the balloon.

In accordance with an exemplary embodiment, a balloon wrapping method is disclosed for wrapping a balloon of a balloon catheter provided with the balloon at a distal portion of an elongated shaft, the balloon wrapping method including: a step of forming the balloon with wing shapes projecting in radial directions; and a step of folding the wing shapes formed in the balloon along a circumferential direction, in which in at least one of the step of forming the wing shapes and the step of folding the wing shapes along the circumferential direction, a part of the balloon catheter which part is on a distal side of the balloon is grasped and a pulling force is applied to the balloon catheter in a state in which the position of the shaft is maintained.

In accordance with an exemplary embodiment, since the balloon wrapping apparatus configured as above-mentioned has the grasping section that grasps a part of the balloon catheter which part is on the distal side of the balloon, it is possible to restrain bending of the balloon catheter due to its own weight from being generated, and to accurately position the balloon in relation to the pleating section and the folding section. Therefore, the wing shapes of the balloon can be formed uniformly in the circumferential direction at the pleating section, and back folding can be restrained from occurring when the wing shapes are folded at the folding section.

When the grasping section has a grasping surface formed of a recessed curved surface, the balloon catheter can be restrained from being damaged when grasped by the grasping section, and, since a larger contact surface can be realized, a high grasping force can be produced.

When the support base has a holding portion for holding the shaft, it is possible to hold the shaft and to maintain the position of the shaft in an appropriate manner. Therefore, the balloon can be accurately positioned in relation to the pleating section and the folding section.

When the balloon wrapping apparatus has a pulling section that applies a pulling force to the balloon catheter by moving the grasping section and the holding portion away from each other, bending of the balloon catheter due to its own weight can be restrained from occurring, by the pulling force. Therefore, the balloon can be accurately positioned in relation to the pleating section and the folding section.

When the balloon wrapping apparatus has a core metal member that is inserted in the shaft, a distal portion of the shaft inclusive of the balloon is supported by the core metal member in such a manner as not to bend. Therefore, the balloon can be accurately positioned in relation to, and inserted into, the pleating section and the folding section.

In the balloon wrapping method configured as above-mentioned, in accordance with an exemplary embodiment, a pulling force is applied to the balloon catheter at the time of forming the balloon with the wing shapes and at the time of folding the wing shapes. Therefore, the balloon catheter can be restrained from bending due to its own weight. For this reason, the balloon can be accurately positioned in a position suitable for forming the balloon with the wing shapes or a position suitable for folding the wing shapes, and the wing shapes of the balloon can be formed uniformly in the circumferential direction or the wing shapes can be folded in a suitable direction.

The pulling force applied to the balloon catheter may be applied by pulling the balloon catheter with a force, for example, of not less than 0.5 N (newton). As a result of this, bending of the balloon catheter due to its own weight can be suitably restrained from occurring.

The pulling force applied to the balloon catheter may be applied by grasping a distal portion of the balloon catheter and moving the distal portion of the balloon catheter, for example, by not less than 1 mm. As a result of this, bending of the balloon catheter due to its own weight can be suitably restrained from occurring.

A balloon wrapping apparatus is disclosed for wrapping a balloon of a balloon catheter arranged with the balloon at a distal portion of an elongated shaft, the balloon wrapping apparatus comprising: a pleating section having a plurality of blades aligned with spaces therebetween in a circumferential direction, and configured to form the balloon with wing shapes projecting in radial directions by rotating the blades of the pleating section; a folding section having a plurality of blades aligned in a circumferential direction, and configured to fold the wing shapes formed in the balloon in the circumferential direction by rotating the blades of the folding section; a support base configured to support a part of an elongated shaft which part is on a proximal side of the balloon; and a grasping section configured to grasp a part of the balloon catheter, which part is on a distal side of the balloon.

BRIEF DESCRIPTION OF THE DRAWINGS

FIGS. 17-19 are Tables 1-3, which illustrate examples of the present disclosure and comparative examples as described herein, which includes drug-coated balloons of Examples 1 to 4 and Comparative Examples 1 to 9 produced under the conditions as set forth in Tables 1-3.

FIG. 20 is Table 4, which compares Comparative Examples 1-5, 7, and 8 to one another including amounts of paclitaxel per unit area after coating and after folding, and a retention rate of paclitaxel for each of the Comparative Examples.

FIG. 21 is Table 5, which depicts the number of drug-coated balloons in which back folding was generated, the total number of drug-coated balloons subjected to folding, and generation rate of back folding for Comparative Examples 4 and 9.

DETAILED DESCRIPTION

Figure 1:
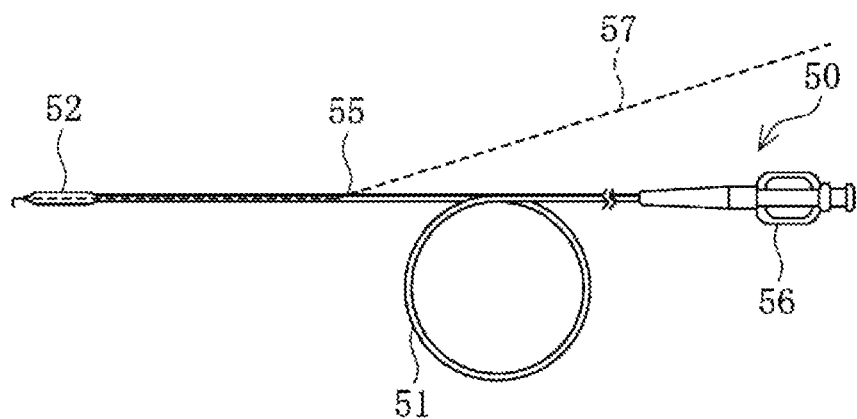
FIG. 1 is a front view of a rapid exchange type balloon catheter.

An exemplary embodiment of the present disclosure will be described below, referring to the drawings. Note that the dimensional ratios in the drawings may be exaggerated and be different from the actual ratios, for convenience of explanation. Herein, the side of insertion of a balloon catheter 50 into a body lumen will be referred to as "distal end" or "distal side," and the side of an operator's hand operation will be referred to as "proximal end" or "proximal side."

A balloon wrapping apparatus according to the present exemplary embodiment is an apparatus capable of wrapping a balloon so as to wrap the balloon around a shaft, at the time of manufacturing a balloon catheter having a balloon at a distal portion of an elongated shaft.

In accordance with an exemplary embodiment, the balloon catheter to be wrapped may be subjected to hydrophilic coating for the purpose of improving properties for delivery to a lesion part, or may have a balloon surface subjected to a surface treatment such as a plasma treatment or irradiation with UV rays, but this is not particularly restrictive. There can also be used a balloon catheter in which the surface of a balloon has been subjected to a drug coating for delivery of a drug to a lesion part.

Figure 2:
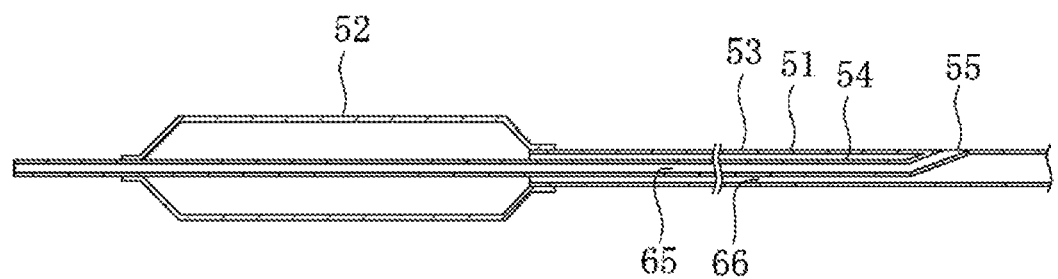
FIG. 2 is a sectional view of a distal portion of the balloon catheter.

In the first place, a balloon catheter 50 will be described. As depicted in FIGS. 1 and 2, the balloon catheter 50 includes an elongated hollow shaft 51, a balloon 52 provided at a distal-side end portion of the shaft 51, and a hub 56 secured to a proximal-side end portion of the shaft 51. The length of the balloon 52 in a major axis direction is not particularly limited, and is greater than, for example, approximately 3 mm. Preferably, the length of the balloon in the major axis direction, for example, is approximately 20 to 400 mm, more preferably 30 to 300 mm, and further preferably approximately 40 to 200 mm.

The diameter of the balloon 52 in a minor axis direction (the direction orthogonal to the major axis direction) is not particularly restricted, and is preferably, for example, not less than 1 mm, more preferably 1 to 10 mm, still more preferably 2 to 8 mm, and further preferably 2 to 4 mm. The material of the balloon 52 is not specifically restricted so long as it is flexible, and is composed, for example, of one or more of polyamides and polyamide elastomers. The surface of the balloon 52 preferably has a smooth surface, but it may not necessarily be smooth. The surface of the balloon 52, for example, may have minute (extremely small) pores that do not penetrate the film, but may not necessarily have minute pores.

The shaft 51 includes a hollow outer tube 53 and a hollow inner tube 54. The inner tube 54 is accommodated in the hollow inside of the outer tube 53, and the shaft 51 has a double-tube structure at its distal portion. The hollow inside of the inner tube 54 is a guide wire lumen 65 in and through which a guide wire 57 is to be inserted and passed. In addition, an inflation lumen 66 through which an inflation fluid for the balloon 52 is permitted to flow is formed in the hollow inside of the outer tube 53 and on the outside of the inner tube 54. The inner tube 54 is open to the exterior at an opening portion 55.

The inner tube 54 protrudes to the distal side beyond a distal end of the outer tube 53. The balloon 52 has a proximal-side end portion fixed to a distal portion of the outer tube 53, and has a distal-side end portion fixed to a distal portion of the inner tube 54. As a result of this, the inside of the balloon 52 communicates with the inflation lumen 66. The balloon 52 can be inflated by injecting an inflation fluid into the balloon 52 through the inflation lumen 66. The inflation fluid may be either a gas or a liquid; for example, a gas such as helium gas, $CO_2$ gas and $O_2$ gas or a liquid such as a saline solution and a contrast medium can be used as the inflation fluid.

In accordance with an exemplary embodiment, the outer tube 53 and the inner tube 54 are preferably formed from a material that has a certain degree of flexibility. Examples of such a material include polyolefins such as polyethylene, polypropylene, polybutene, ethylene-propylene copolymer, ethylene-vinyl acetate copolymer, ionomers, or mixtures of two or more of them, flexible polyvinyl chloride resin, polyamides, polyamide elastomers, polyesters, polyester elastomers, polyurethane, fluoro-resin such as polytetrafluoroethylene, silicone rubbers, and latex rubbers.

Where the balloon catheter 50 is used in such a manner that the elongated shaft 51 of the balloon catheter 50 is inserted into a body organ and the balloon 52 provided on the distal side thereof is inflated at a lesion part, it is possible to push open the lesion part and thereby to perform a treatment. The shaft 51 is provided, at a position near the distal side, with the opening portion 55 through which to introduce the guide wire 57. In other words, this balloon catheter 50 is a so-called rapid exchange type catheter.

Figure 3:
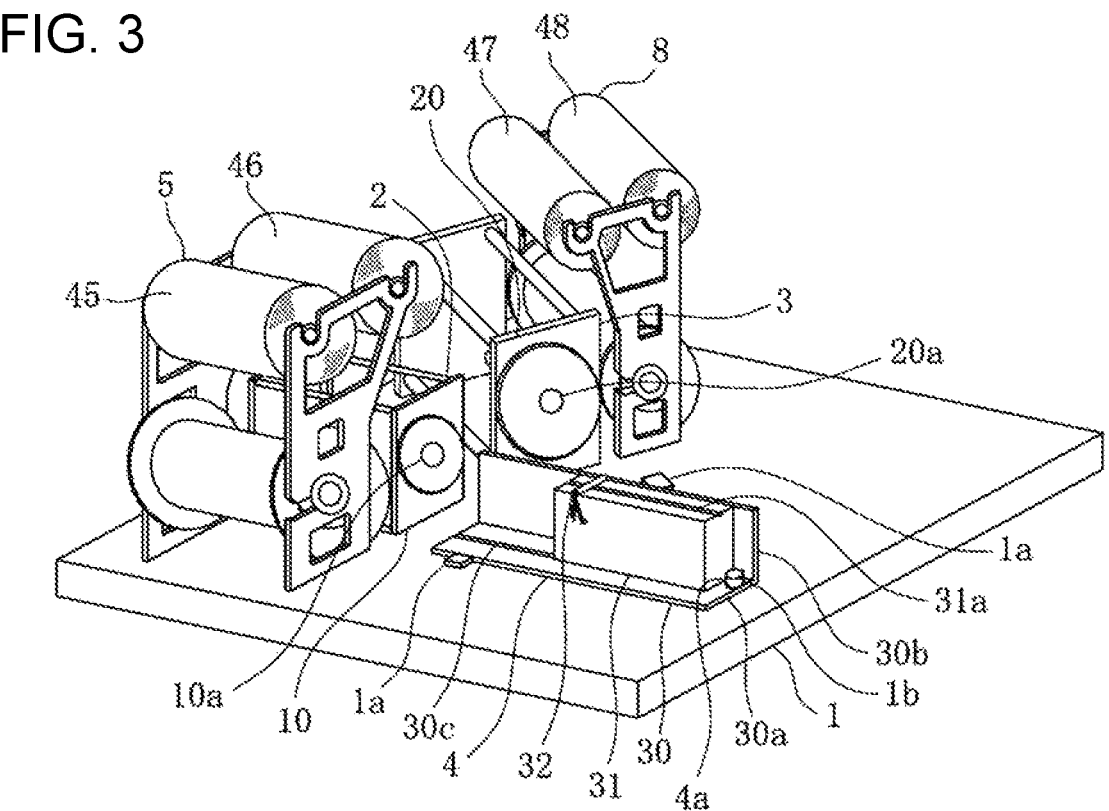
FIG. 3 is a perspective view of a balloon wrapping apparatus according to the present embodiment.

In the next place, the balloon wrapping apparatus will be described. As depicted in FIG. 3, the balloon wrapping apparatus has a pleating section 2, a folding section 3 and a support base 4 disposed on a base 1 formed in a base shape. The pleating section 2 is capable of forming a balloon 52 with wing shapes projecting in radial directions. The folding section 3 is capable of folding the wing shapes formed in the balloon 52 in the manner of laying the wing shapes flat in a circumferential direction. The support base 4 is capable of disposing and holding the balloon catheter 50 thereon. The wing shapes formed in the balloon 52 are formed of pleats of balloon thin film material having a length extending substantially in a major axis direction of the balloon 52, and are so formed that the pleats project in the circumferential direction from the major axis of the balloon 52, as viewed in a section perpendicular to the major axis of the balloon 52. The length of the wing shapes in the major axis direction does not exceed the length of the balloon 52, and can be, for example, approximately 3 mm to 400 mm, preferably approximately 3 mm to 300 mm, more preferably approximately 30 mm to 300 mm, and further preferably approximately 40 mm to 200 mm in length. The length by which the wing shape projects in the circumferential direction from the shaft 51 can be, for example, 1 mm to 8 mm. The number of the wing shapes is not particularly limited, and can be selected from among two, three, four, five, six and seven. In this embodiment, three wing shapes are adopted.

A film supplying section 5 for supplying a first film 45 and a second film 46 to the pleating section 2 is disposed on the base 1, adjacently to the pleating section 2. In addition, a film supplying section 8 for supplying a first film 47 and a second film 48 to the folding section 3 is disposed on the base 1, adjacently to the folding section 3.

The pleating section 2 has a front surface plate 10 perpendicular to the base 1, and the front surface plate 10 has an insertion hole 10a through which a distal portion of the balloon catheter 50 can be inserted. In addition, the folding section 3 has a front surface plate 20 perpendicular to the base 1, and the front surface plate 20 has an insertion hole 20a through which the distal portion of the balloon catheter 50 can be inserted. The front surface plate 20 of the folding section 3 is oriented in a direction different by a predetermined angle from a direction in which the front surface plate 10 of the pleating section 2 is oriented.

The support base 4 is formed, on the side remote from the pleating section 2 and the folding section 3, with a hole 4a in which a support rod 1b projecting upward from the base 1 is pivotally fitted. By being slid on an upper surface of the base 1 with the support rod 1b as a center, the support base 4 can be positioned in a position for facing the front surface plate 10 of the pleating section 2 and in a position for facing the front surface plate 20 of the folding section 3.

In accordance with an exemplary embodiment, two positioning sections 1a capable of positioning the support base 4 to be oriented in two different directions are provided on the base 1. In FIG. 3, the support base 4 is positioned in contact with the positioning section 1a projecting from the base 1, in such a manner as to face the front surface plate 10 of the pleating section 2. The support base 4 can also be positioned such as to face the front surface plate 20 of the folding section 3, by putting the support base 4 in contact with the positioning section 1a on the other side.

The support base 4 includes a base section 30 placed on the base 1, and a holding base section 31 which can be moved horizontally on the base section 30. The base section 30 includes a bottom surface portion 30a placed on an upper surface of the base 1 and positioned by the positioning section 1a, and a side surface portion 30b extending vertically upward from a side portion of the bottom surface portion 30a. A slide guide portion 30c for guiding a sliding movement of the holding base section 31 toward the pleating section 2 or the folding section 3 is formed at an upper surface of the bottom surface portion 30a.

Figure 4:
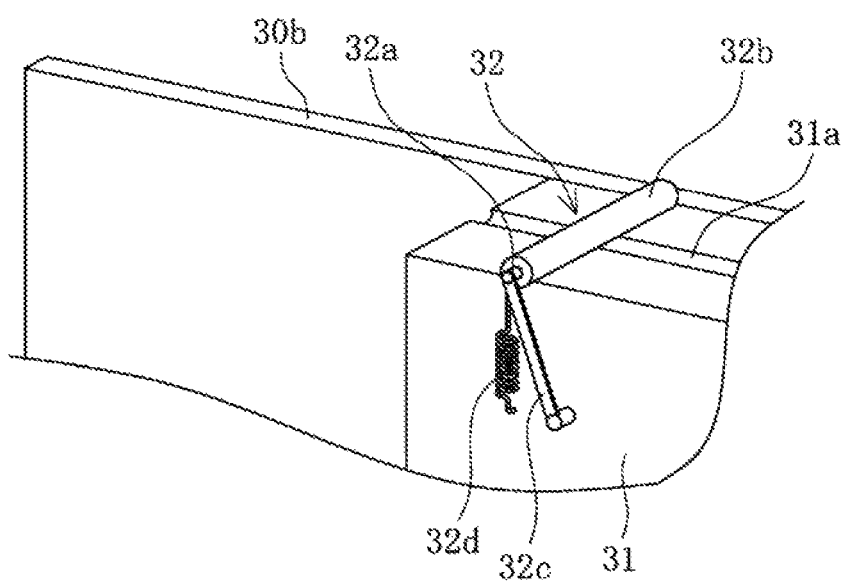
FIG. 4 is an enlarged perspective view of a holding base section of the balloon wrapping apparatus.

As depicted in FIGS. 3 and 4, the holding base section 31 is formed substantially in the shape of a rectangular parallelepiped which makes contact with the bottom surface portion 30a and the side surface portion 30b of the base section 30. A lower surface of the holding base section 31 is slidably guided by the slide guide portion 30c of the bottom surface portion 30a. In addition, an upper surface of the holding base section 31 has a groove-shaped placing portion 31a on which the shaft 51 of the balloon catheter 50 can be placed. In accordance with an exemplary embodiment, the holding base section 31 is provided with a holding portion 32 such as to cover from above a part of the placing portion 31a. The holding portion 32 is capable of holding, and thereby fixing, the shaft 51 of the balloon catheter 50 placed on the placing portion 31a. The holding portion 32 includes a holding rod 32a intersecting the placing portion 31a, a flexible contact portion 32b covering the holding rod 32a, a rotational support portion 32c for supporting the holding rod 32a rotatably in relation to the holding base section 31, and a coil 32d (elastic member) for pressing the contact portion 32b against the placing portion 31a by rotating the rotational support portion 32c. With the contact portion 32b moved away from the placing portion 31a in such a manner as to stretch the coil 32d, the shaft 51 can be placed on the placing portion 31a. With the contact portion 32b put into contact with the shaft 51 in a state in which the shaft 51 is placed on the groove-shaped placing portion 31a, the shaft 51 can be held by a pressing force of the coil 32d. In this instance, since the contact portion 32b is flexible, the shaft 51 can be suitably held without damage. Note that a flexible material may be disposed in a region in which the shaft 51 is pressed by the contact portion 32b, of the placing portion 31a. In addition, in the present embodiment, as depicted in FIG. 4, the shaft 51 is fixed from above by the holding portion 32 that intersects the shaft 51, but the fixation may be conducted by another method so long as the shaft 51 can be fixed. For example, the shaft 51 of the balloon 52 may be fixed by sandwiching the shaft 51 in the manner of putting flexible materials such as silicone resin into contact with the surface of the shaft 51, from both sides in a direction substantially perpendicular to the axis of the shaft 5. In fixing the shaft 51 by sandwiching it with flexible materials, the sandwiching may be conducted by applying attractive forces of magnets. In addition, the core metal member 6 in the shaft 51 may be formed of a magnetic material, and the core metal member 6 may be fixed by magnets.

In accordance with an exemplary embodiment, the core metal member 6 is formed in a thin elongated wire-like shape or a hollow shape from a metallic material. As the metallic material for forming the core metal member 6, there is selected a material having such a degree of harness that a distal portion of the shaft 51 inclusive of the balloon 52 will not bend due to its own weight where the core metal member 6 is inserted in the balloon 52 and the shaft 51. The metallic material for forming the core metal member 6 is not specifically restricted, and examples thereof include stainless steel, Ni—Ti alloys, tungsten, and hard metals. In addition, the core metal member 6 may be formed by annealing any of these metallic materials, for realizing a shape memory property.

The core metal member 6 is formed in a substantially circular shape in section, and an outside (or outer) diameter of the core metal member 6 can be equal to an inside (or inner) diameter of the inner tube 54 or smaller than the inside (or inner) diameter, for example, by 0.01 mm to 0.1 mm. If the outside diameter of the core metal member 6 is smaller than the aforesaid appropriate value in relation to the inside diameter of the inner tube 54, the balloon 52 part cannot be held sufficiently by the core metal member 6, and bending of the balloon 52 would occur. As a result, the shaft 51 may be distorted when the balloon 52 is formed with wing shapes by the pleating section 2. In accordance with an exemplary embodiment, if the outside shape of the core metal member 6 is greater than the aforesaid appropriate value in relation to the inside diameter of the inner tube 54, the core metal member 6 may interfere with the inner surface of the inner tube 54, possibly breaking the inner tube. With the outside diameter of the core metal member 6 set as above-mentioned, these problems can be prevented from occurring.

In a state in which the support base 4 faces the front surface plate 10 of the pleating section 2, the center of the insertion hole 10a formed in the front surface plate 10 is located on an extension line of the placing portion 31a of the holding base section 31. Therefore, the balloon catheter 50 having the shaft 51 placed on the placing portion 31a is inserted into the pleating section 2 through the center position of the insertion hole 10a. In a state in which the support base 4 faces the front surface plate 20 of the folding section 3, the center of the insertion hole 20a formed in the front surface plate 20 is located on an extension line of the placing portion 31a of the holding base section 31. For this reason, the balloon catheter 50 having the shaft 51 placed on the placing portion 31a is inserted into the folding section 3 through the center position of the insertion hole 20a by slidably moving the holding base section 31 on the base section 30.

Figure 5:
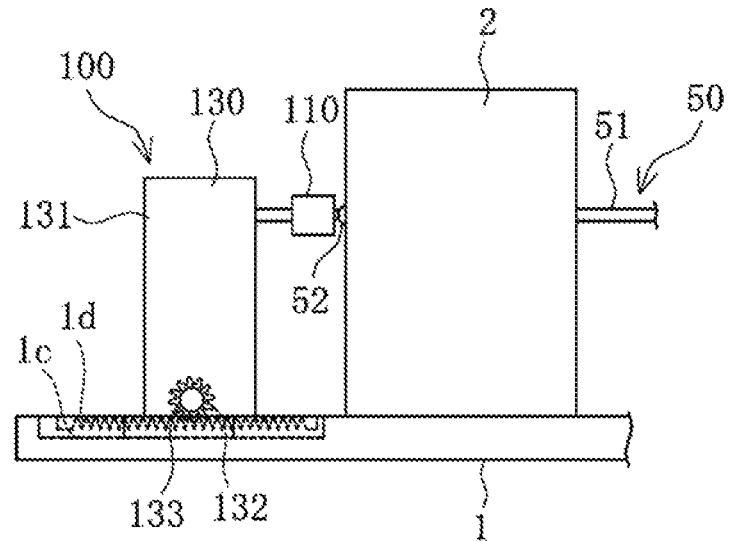
FIG. 5 is a front view of a traction section.

As depicted in FIG. 5, a traction section 100 for grasping and pulling a part of the balloon catheter 50 which part is on the distal side of the balloon 52 is provided on a side of the pleating section 2 and the folding section 3 which side is opposite to the side of facing the support base 4. The traction section 100 includes a grasping section 110 for grasping a part of the balloon catheter 50, which part is on the distal side of the balloon 52, and a pulling section 130 for applying a pulling force to the balloon catheter by moving the grasping section 110.

In accordance with an exemplary embodiment, the pulling section 130 can include a sliding portion 131 fitted to a guide groove portion 1c formed in the base 1, a pinion 132 meshing with a rack 1d having teeth arranged rectilinearly on the base 1, and a dial 133 for rotating the pinion 132. The sliding portion 131 is a portion to which the grasping section 110 is interlocked, and which is slidably fitted in the guide groove portion 1c of the base 1. By sliding in the guide groove portion 1c, the sliding portion 131 moves the grasping section 110 rectilinearly. The pinion 132 is rotated by rotating the dial 133, and, by meshing with the rack 1d, the pinion 132 moves the sliding portion 131 along the guide groove portion 1c. Therefore, with the dial 133 rotated, the pulling section 130 can move the grasping section 110 rectilinearly, thereby applying a pulling force to the balloon catheter 50 grasped by the grasping section 110. With the pulling force applied to the balloon catheter 50, the balloon catheter 50 can be restrained from bending due to its own weight.

Figure 6:
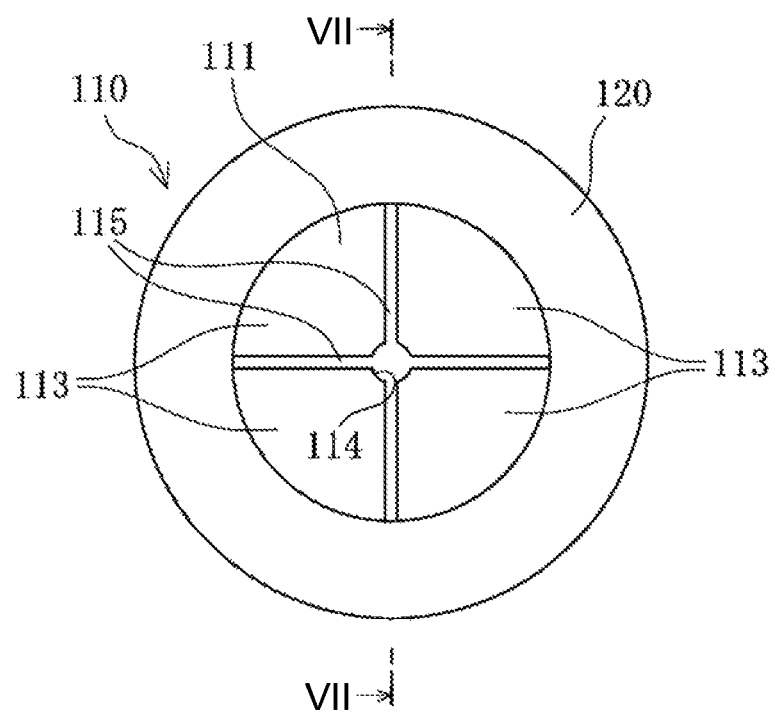
FIG. 6 is a front view of a grasping section.
Figure 7:
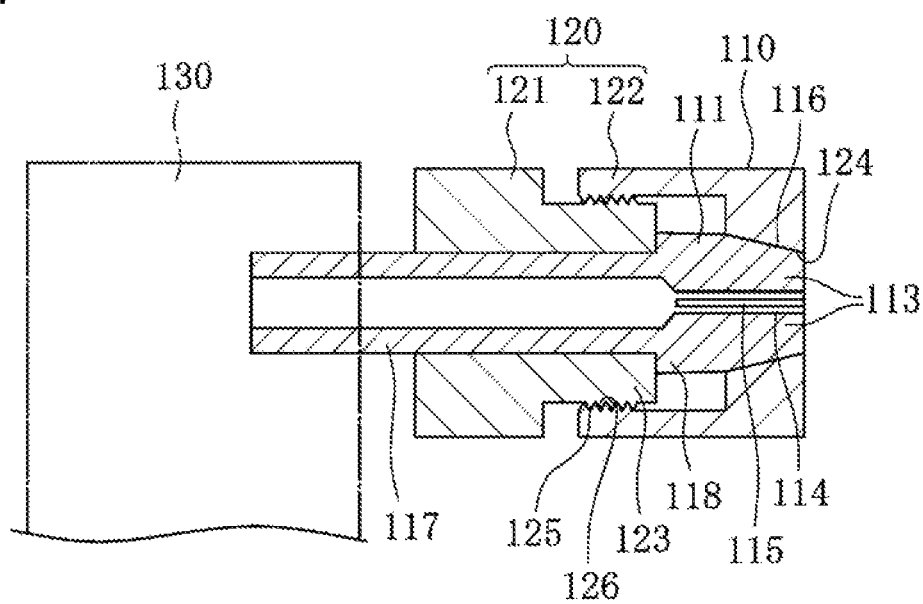
FIG. 7 is a sectional view taken along line VII-VII of FIG. 6.

As depicted in FIGS. 5 to 7, the grasping section 110 can include a collet chuck 111 and a chuck holder 120 for holding the collet chuck 111.

The collet chuck 111 is formed with slits 115 in such a manner that a plurality (for example, in the present embodiment, four) of clamping portions 113 having clamping surfaces 114 shaped in conformity with the shape of an object to the grasped are aligned in a circumferential direction. The collet chuck 111 is formed with a tapered surface 116 at an outer circumferential surface on the side of an end portion where the clamping portions 113 are formed, and is formed with an interlock portion 117 for interlock with the pulling section 130 on the side opposite to the side where the clamping portions 113 are formed. The interlock portion 117 is formed to be smaller than the clamping portions 113 in outside diameter. A stepped portion 118 where the outside diameter is reduced is formed between the clamping portions 113 and the interlock portion 117. The clamping surfaces 114 are formed of groove-shaped curved surfaces extending along the axis of the balloon catheter 50, and can grasp the balloon catheter 50 on a surface basis such as to prevent, as securely as possible, deformation of the balloon catheter 50. Note that a scroll chuck, a drill chuck or an independent chuck may be used in place of the collet chuck 111. In addition, the number of the clamping portions need only be two or more, and is not limited to four.

Figure 8:
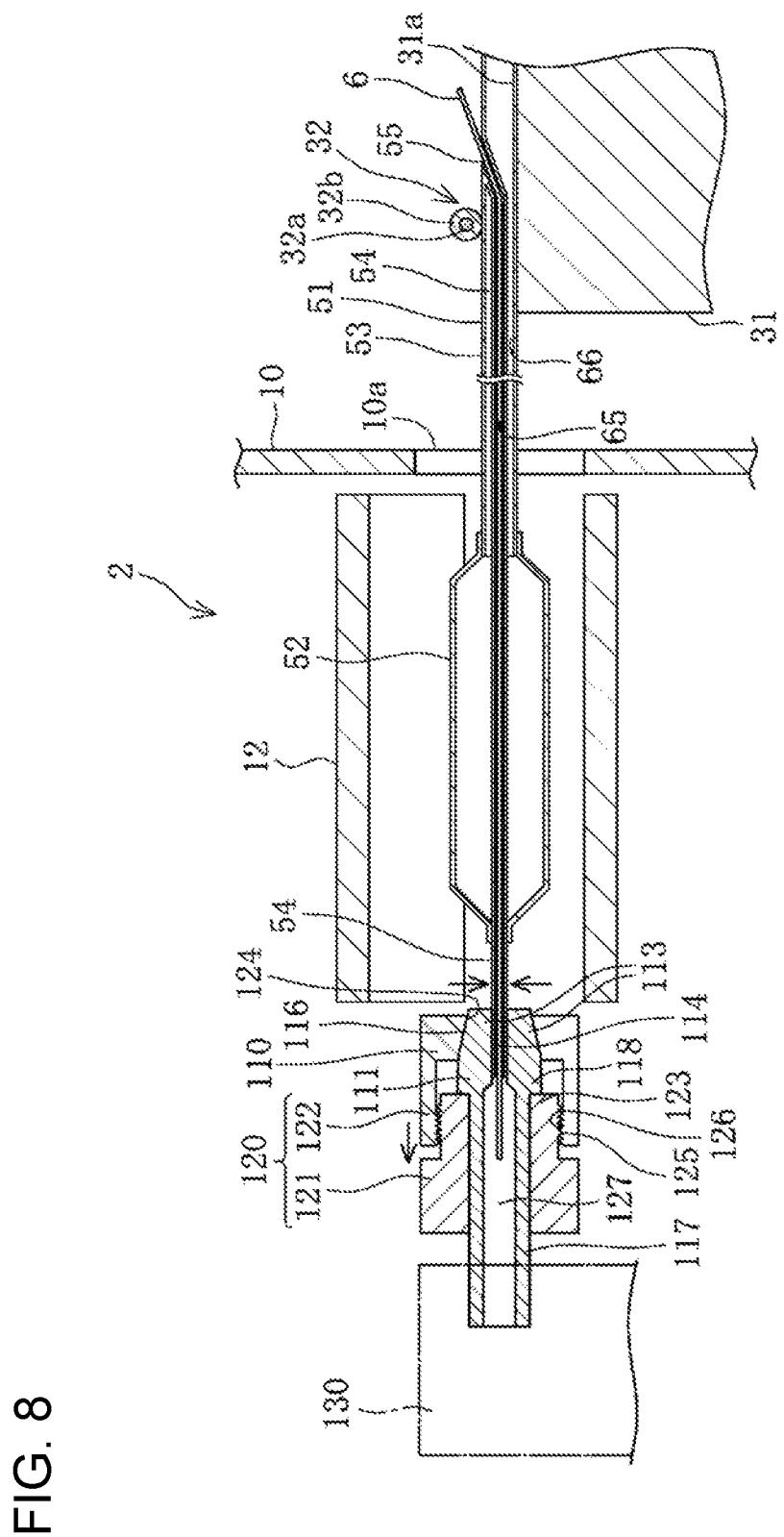
FIG. 8 is a sectional view of a balloon catheter disposed in a pleating section.

In accordance with an exemplary embodiment, the chuck holder 120 can include a first holder 121 which the interlock portion 117 of the collet chuck 111 penetrates, and a second holder 122 with which the clamping portions 113 of the collet chuck 111 make contact. The first holder 121 is a tubular member which the interlock portion 117 of the collet chuck 111 penetrates, and is provided on one end side thereof with a contact portion 123 capable of making contact with the stepped portion 118 of the collet chuck 111 in such a manner that the stepped portion 118 is caught thereon, and an outer circumferential surface of the contact portion 123 is formed with a first screw portion 125. The second holder 122 is a tubular member having a second screw portion 126 screw engaged with the first screw portion 125, and is formed at an inner circumferential surface thereof with a tapered pressing-in surface 124 making contact with the tapered surface 116 of the chuck holder 120. When the collet chuck 111 is disposed inside the first holder 121, the stepped portion 118 is put in contact with the contact portion 123, the second screw portion 126 of the second holder 122 is screw engaged with the first screw portion 125 of the first holder 121, and the second holder 122 is rotated, as depicted in FIG. 8, the second holder 122 is moved in the direction of coming closer to the first holder 121. When the second holder 122 is moved in the direction of coming closer to the first holder 121, the pressing-in surface 124 of the second holder 122 slides on the tapered surface 116 of the collet chuck 111, and the clamping portions 113 are deformed in such a manner that the slits 115 are narrowed, so that the clamping surfaces 114 come closer to one another. As a result of this, a distal portion of the balloon catheter 50 can be clamped in the center of the clamping surfaces 114. Note that the part clamped by the clamping portions 113 need only be a part on the distal side of the inflating portion of the balloon 52, and may be either the inner tube 54 (and the core metal member 6) or that part (and the core metal member 6) of a distal portion of the balloon 52 which is joined to the inner tube 54.

Examples of the material or materials, which can be used for constituting the collet chuck 111 and the chuck holder 120 include metals such as stainless steel and aluminum, and resins such as fluoro-resins, acrylonitrile-butadiene-styrene resin, and polyethylene.

When the balloon catheter 50 is grasped by the collet chuck 111, the core metal member 6 is disposed inside the guide wire lumen 65 such that the balloon catheter 50 will not be crushed. In accordance with an exemplary embodiment, the core metal member 6 preferably has its distal portion protruding to the distal side beyond the guide wire lumen 65, and preferably has its proximal portion protruding from the opening portion 55.

Figure 9:
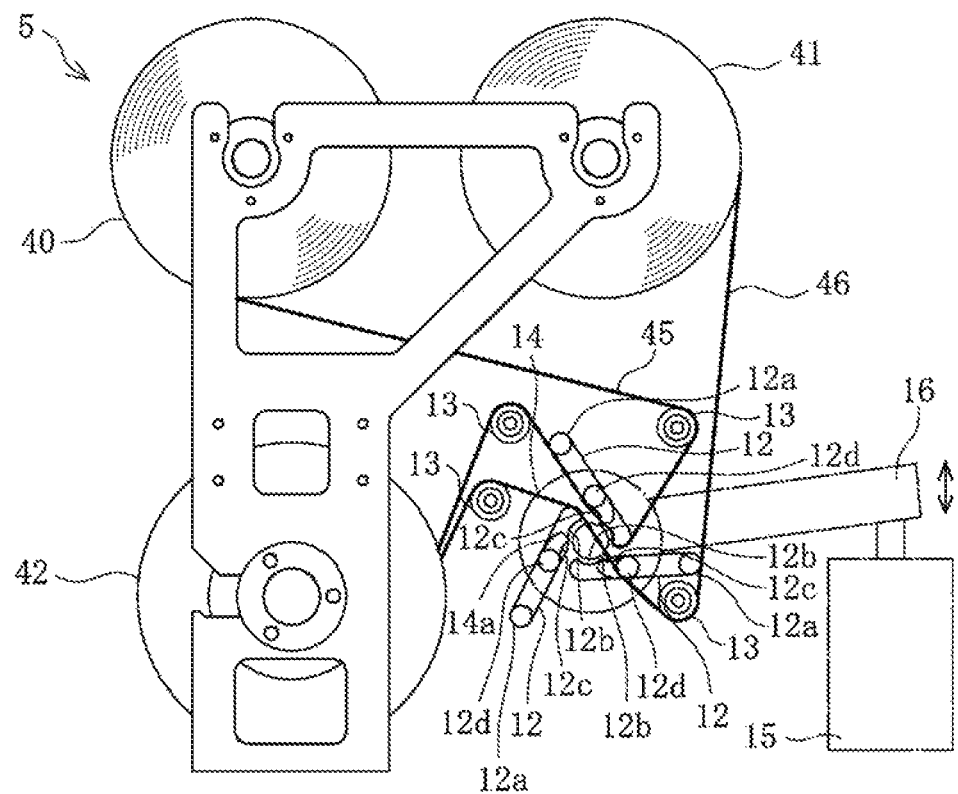
FIG. 9 is a front view depicting the layout of blades of the pleating section and a film supplying section.

Now, the structure of the pleating section 2 will be described below. As illustrated in FIG. 9, the pleating section 2 is provided therein with three blades 12 (wing forming members). Each of the blades 12 can be a plate-shaped member which is the same in sectional shape at each position along the axial direction of the balloon catheter 50 inserted. The blades 12 are disposed such that they are at an angle of 120° from one another, with the center position in regard of insertion of the balloon 52 as a reference. In accordance with an exemplary embodiment, the blades 12 are disposed at regular angular intervals along the circumferential direction. The blade 12 has a rotational center portion 12a near an outer circumferential end portion thereof, and can be moved rotationally about the rotational center portion 12a. In addition, the blade 12 has a moving pin 12d extending in the axial direction, on the inner circumferential side of the rotational center portion 12a. The moving pin 12d is fitted in a fitting groove 14a formed in a rotary member 14 which is rotatable in the pleating section 2. The rotary member 14 is interlocked with a beam portion 16 extending substantially horizontally. The rotary member 14 is movable rotationally by receiving a rotating force from the beam portion 16 which is inclined by receiving a force from a drive source 15 such as a hydraulic cylinder or a motor. When the rotary member 14 is rotated, the moving pins 12d fitted in the fitting grooves 14a are moved in the circumferential direction, whereby each of the blades 12 is moved rotationally about the rotational center portion 12a. With the three blades 12 rotated, a space region in a central area surrounded by the blades 12 can be narrowed. Note that the number of the blades 12 need only be two or more, and is not particularly limited.

The blade 12 has a first shape forming portion 12b and a second shape forming portion 12c which are substantially arcuate in shape, at inner circumferential end portions on the side opposite to the rotational center portion 12a. Attendant on rotary movement of the blade 12, the first shape forming portion 12b makes contact with the surface of the balloon 52 inserted in the pleating section 2, whereby the balloon 52 can be formed with a wing shape projecting in a radial direction. Attendant on rotary movement of the blade 12, the second shape forming portion 12c makes contact with the wing portion formed in the balloon 52, whereby the wing shape can be curved in a predetermined direction. In addition, the pleating section 2 has a heater (not depicted) for heating the blades 12. Note that the blades 12 may have a function of cooling. The length of the blade 12 along the axial direction of the balloon catheter 50 is greater than the length of the balloon 52. In addition, the lengths of the first shape forming portion 12b and the second shape forming portion 12c of the blade 12 may or may not range over the whole length of the blade 12.

In accordance with an exemplary embodiment, the blades 12 are supplied with the first film 45 and the second film 46 which are formed of resin, from the film supplying section 5. For guiding each of the films 45, 46, a plurality of rotary shaft portions 13 are provided in the pleating section 2. The first film 45 is supplied from a first film holding section 40 and through the rotary shaft portion 13 to be fed to a surface of the blade 12 disposed at an upper part. In addition, the first film 45 is fed through the blade 12 and the rotary shaft portion 13 to reach a film take-up section 42 which is rotationally driven by a drive source (not depicted) such as a motor. The second film 46 is supplied from a second film holding section 41 and through the rotary shaft portion 13 to be fed to the two blades 12 disposed at lower parts. In addition, the second film 46 is fed through the rotary shaft portion 13 to reach the film take-up section 42. As a result of these, a center position of the pleating section 2 in which the balloon 52 is inserted is in the state of being surrounded by the first film 45 and the second film 46.

The first film 45 and the second film 46 have a protecting function for preventing direct contact of the balloon 52 with the surfaces of the blades 12 when the balloon 52 is inserted into the pleating section 2 and the blades 12 are moved rotationally to form the balloon 52 with wing shapes. After the wing shapes of the balloon 52 are formed, predetermined lengths of the first film 45 and the second film 46 are taken up by the film take-up section 42. In other words, the portions of the first film 45 and the second film 46 which portions have once made contact with the balloon 52 do not make contact with the balloon 52 again, and new portions of the films are supplied to the center position of the pleating section 2 every time the balloon 52 is inserted.

Figure 10:
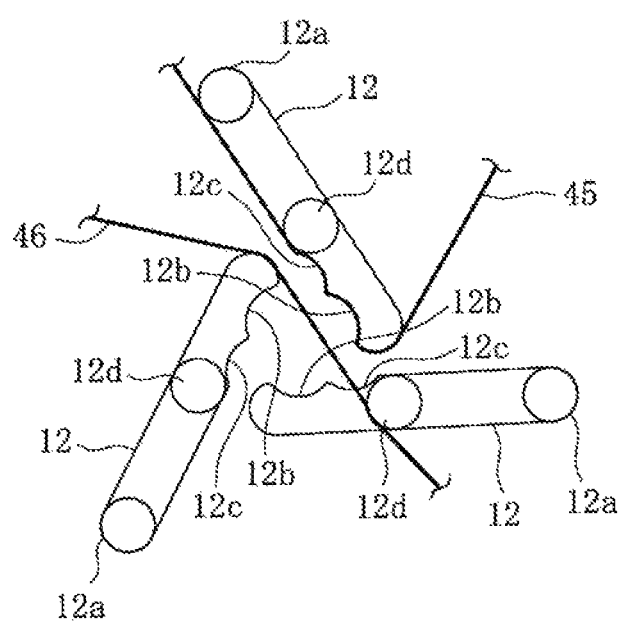
FIG. 10 is a front view of the blades in the pleating section.

As depicted in FIG. 10, in a state before insertion of the balloon 52, the first shape forming portions 12b and the second shape forming portions 12c of the three blades 12 are in the state of being spaced from one another. A central region between the blades 12 is surrounded by the substantially arcuate first shape forming portions 12b, and the balloon 52 yet to be wrapped can be inserted therein.

In forming the balloon 52 with wing shapes, first, the shaft 51 of the balloon catheter 50 is placed on the placing portion 31a of the support base 4 and is held by the holding portion 32. The inflation fluid is injected into the balloon 52 through a three-way cock (valve) attached to the hub 56, the hub 56 and the inner tube 54, whereby the balloon 52 is put into a state of being inflated to a certain extent. In addition, the blades 12 of the pleating section 2 are heated. The core metal member 6 is inserted into the guide wire lumen 65. By the core metal member 6, the shaft 51 is restrained from bending due to its own weight. As a result, the balloon 52 can be inserted, with accurate positioning, into the center position of the pleating section 2.

The core metal member 6 is formed in a thin elongated wire-like shape from a metallic material. The metallic material for forming the core metal member 6 is not specifically restricted, and examples thereof include stainless steel, Ni—Ti alloys, Ni—Ti alloys, tungsten, and hard metals. In addition, the core metal member 6 may be formed by annealing any of these metallic materials, to realize a shape memory property. The core metal member 6 is formed in a substantially circular shape in section, and its outside diameter is smaller than the inside diameter of the inner tube 54, for example, by 0.01 mm to 0.1 mm.

Next, as depicted in FIG. 8, the holding base section 31 is moved by sliding on the base section 30, whereby the balloon catheter 50 is inserted into the pleating section 2 through the insertion hole 10a. In this instance, since the core metal member 6 is inserted in the guide wire lumen 65, the shaft 51 is restrained from bending due to its own weight, and the balloon 52 can be accurately positioned in the center position of the pleating section 2.

Subsequently, a portion of the balloon catheter 50 which portion is on the distal side of the balloon 52 is grasped by the grasping section 110. Thereafter, the dial 133 of the pulling section 130 is rotated, whereon the grasping section 110 is moved rectilinearly, a pulling force is applied to the balloon catheter 50 grasped by the grasping section 110, and bending of the balloon catheter 50 due to its own weight is reduced.

Figure 11:
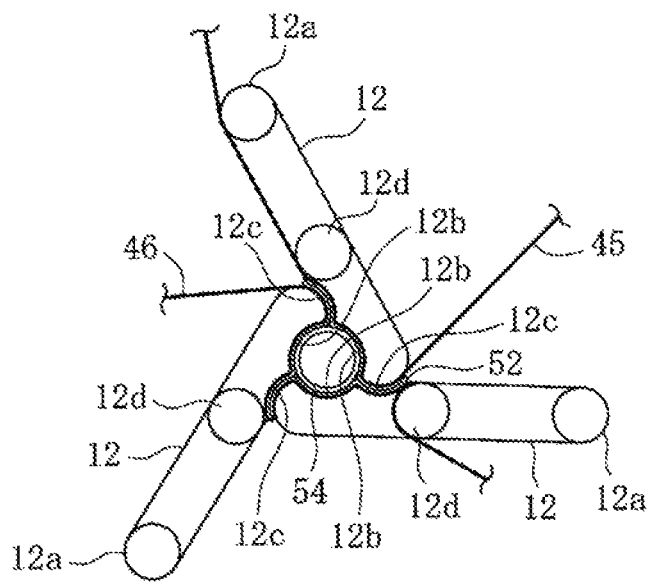
FIG. 11 is a front view of the blades in a state in which the blades are moved rotationally from the state of FIG. 10 to form a balloon with wing shapes.

Next, the rotary member 14 is rotated by operating the drive source 15, whereon the blades 12 are rotated, the first shape forming portions 12b of the blades 12 come closer to one another, and the central region between the blades 12 is narrowed, as depicted in FIG. 11. Attendant on this, the balloon 52 inserted in the central region between the blades 12 is pressed against the inner tube 54 by the first shape forming portions 12b. A portion of the balloon 52 which portion is not pressed by the first shape forming portion 12b is pushed out into a gap between a distal portion of one blade 12 and the second shape forming portion 12c of the blade 12 adjacent to the one blade 12, whereby a wing shape curved to one side is formed. Since the balloon 52 is heated by the blades 12, the wing shapes thus formed can be maintained in their shape. In this way, the balloon 52 is formed with three wing shapes in the circumferential direction. Note that the number of blades 12 is not particularly limited so long as the number of blades 12 is two or more.

In this instance, surfaces of the blades 12 which surfaces make contact with the balloon 52 are covered with the first film 45 and the second film 46, so that the balloon 52 does not make direct contact with the surfaces of the blades 12. After the balloon 52 is formed with the wing shapes, the blades 12 are moved rotationally in the manner of being returned into their original positions, and the balloon 52 is withdrawn from the pleating section 2. Note that in the process of pleating, a step of excessively inflating the balloon 52 and then deflating the balloon 52 a little (or slightly) or a step of inflating the balloon 52 while avoiding excessive inflation and then deflating the balloon 52 a little (or slightly) may be provided.

Figure 12:
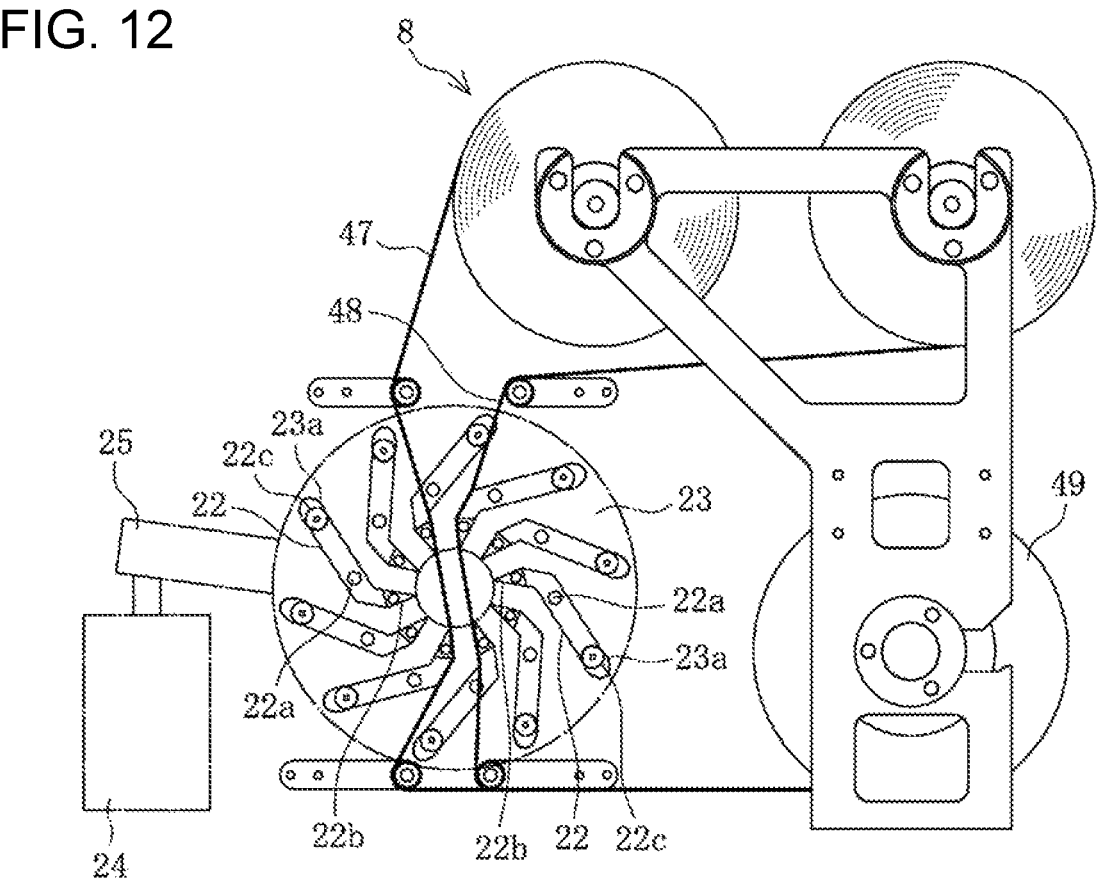
FIG. 12 is a front view depicting the layout of blades in a folding section and the film supplying section.

Now, the structure of the folding section 3 will be described below. As illustrated in FIG. 12, the folding section 3 is provided therein with ten blades 22 (folding members). Each of the blades 22 is a plate-shaped member formed to be the same in sectional shape at each position along the axial direction of the balloon catheter 50 to be inserted. The blades 22 are disposed such that they are at an angle, for example, of 36° from one another, with the center position in regard of insertion of the balloon as a reference. In other words, the blades 22 are disposed at regular angular intervals along the circumferential direction. The blade 22 has a rotational center portion 22a near a substantial center thereof, and can be moved rotationally about the rotational center portion 22a. In addition, the blade 22 has a moving pin 22c extending in the axial direction, near a substantially outer circumferential end portion thereof. The moving pin 22c is fitted in a fitting groove 23a formed in a rotary member 23 which is rotatable in the folding section 3. The rotary member 23 is interlocked with a beam portion 25 extending substantially horizontally. The rotary member 23 is movable rotationally by receiving a rotating force from the beam portion 25 which is inclined by receiving a force from a drive source 24 such as a hydraulic cylinder or a motor. When the rotary member 23 is rotated, the moving pins 22c fitted in the fitting grooves 23a are moved in the circumferential direction, whereby each of the blades 22 is moved rotationally about the rotational center portion 22a. With the ten blades 22 moved rotationally, a space region in a central area surrounded by the blades 22 can be narrowed. Note that the number of the blades 22 is not particularly limited.

The blade 22 is bent on the distal side, and has a distal portion 22b in a pointing (or pointed) shape. Attendant on rotary movement of the blade 22, the distal portion 22b makes contact with a surface of the balloon 52 inserted in the folding section 3, whereby the wing shape formed in the balloon 52 can be folded in the manner of lying flat in the circumferential direction. In addition, the folding section 3 has a heater (not depicted) for heating the blades 22. Note that the blades 22 may have a function of cooling.

The blades 22 are supplied with a first film 47 and a second film 48 from a film supplying section 8. The film supplying structure is the same as in the case of the pleating section 2. The first film 47 and the second film 48 are disposed opposite to each other in such a manner as to sandwich a central space region surrounded by the blades 22. By the first film 47 and the second film 48, the balloon 52 inserted in the folding section 3 can be prevented from making direct contact with the surfaces of the blades 22. The first film 47 and the second film 48 are fed through the blades 22, to reach a film take-up section 49 which is rotationally driven by a drive source (not depicted) such as a motor.

Figure 14:
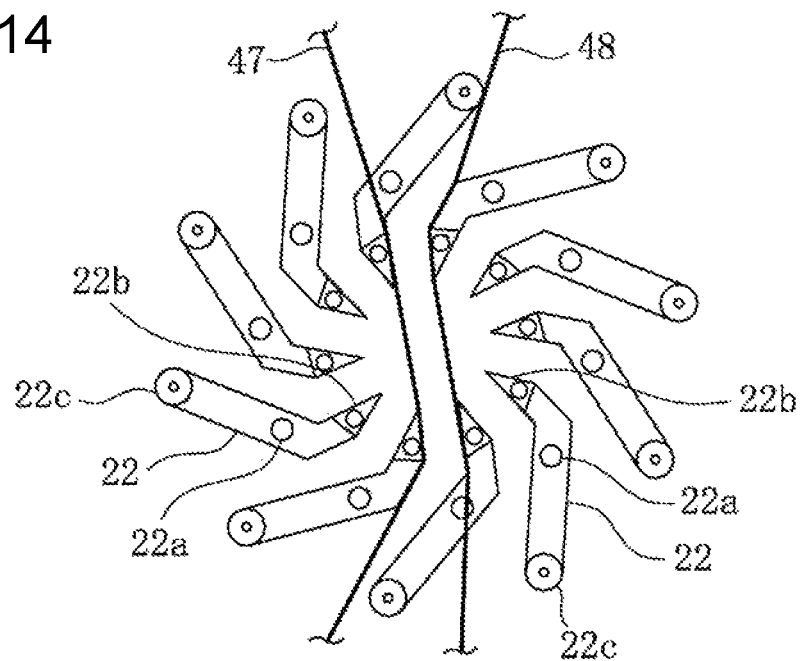
FIG. 14 is a front view of the blades in the folding section.

As depicted in FIG. 14, in a state before insertion of the balloon 52, the distal portions 22b of the blades 22 are in the state of being spaced from one another in a circumferential direction. The balloon 52 formed with the wing shapes can be inserted into a central region which is surrounded by the blades 22 and which is between the first film 47 and the second film 48.

Figure 13:
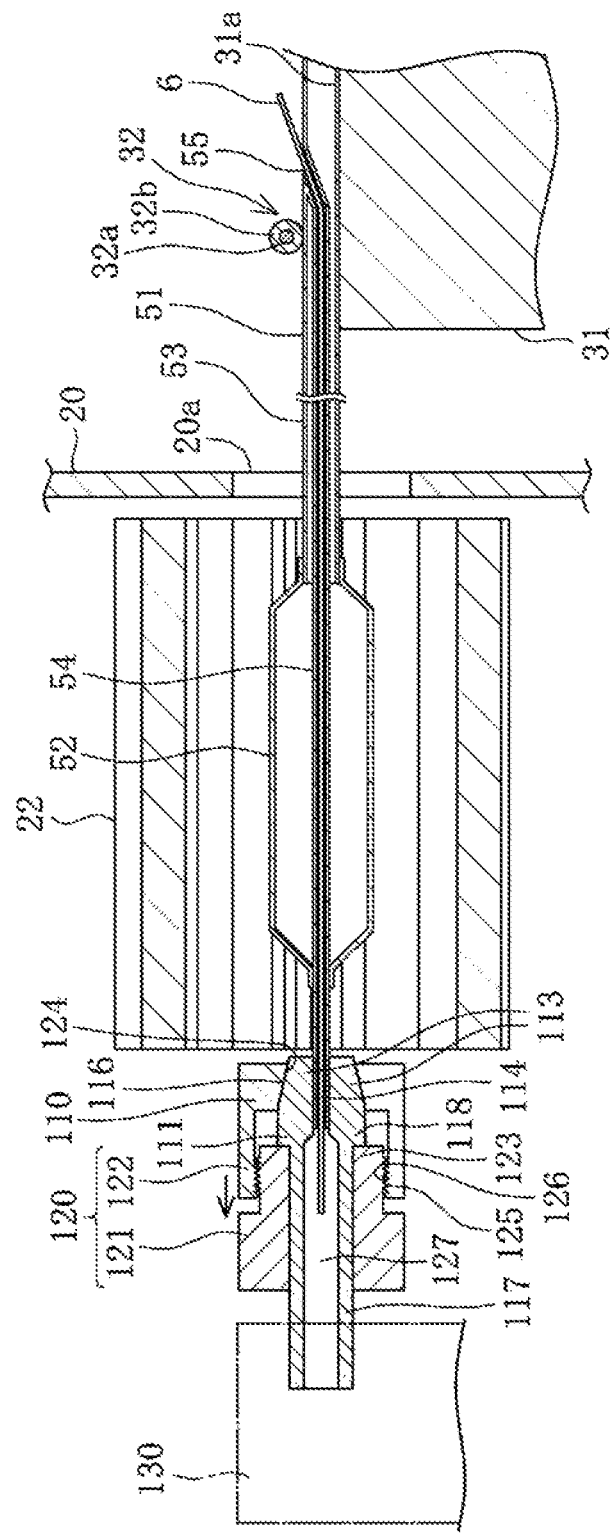
FIG. 13 is a sectional view of a balloon catheter disposed in the folding section.

After the balloon catheter 50 is inserted into the pleating section 2 and the balloon 52 is formed with the wing shapes as aforementioned, the balloon catheter 50 is detached from the grasping section 110 provided in the pleating section 2. Next, the holding base section 31 is moved on an upper surface of the base section 30 to be spaced from the pleating section 2, and the balloon catheter 50 is withdrawn from the pleating section 2. Subsequently, the support base 4 is moved by sliding on the upper surface of the base section 1, to position the support base 4 in a position of facing the front surface plate 20 of the folding section 3. Thereafter, the holding base section 31 is moved on the upper surface of the base section 30, to insert the balloon catheter 50 into the folding section 3 through the insertion hole 20a. In accordance with an exemplary embodiment, the blades 22 of the folding section 3 have already been heated. In addition, the blades 22 may not necessarily be heated, or may be cooled. In this instance, as depicted in FIG. 13, the shaft 51 is maintained in the state of being held by the holding portion 32 of the support base 4. The core metal member 6 is also inserted in the balloon catheter 50, like in the case of insertion into the pleating section 2. Next, a part of the balloon catheter 50 which part is on the distal side of the balloon 52 is grasped by the grasping section 110 provided in the folding section 3. Thereafter, the dial 133 of the pulling section 130 is rotated, whereon the grasping section 110 is moved rectilinearly, and a pulling force is applied to the balloon catheter 50 grasped by the grasping section 110, whereby bending of the balloon catheter 50 due to its own weight can be reduced.

In this way, also in the case where the balloon catheter 50 is inserted into the folding section 3, with the balloon catheter 50 grasped and pulled, the shaft 51 is restrained from bending due to its own weight, and the balloon 52 can be accurately positioned in the center position of the folding section 3.

Figure 15:
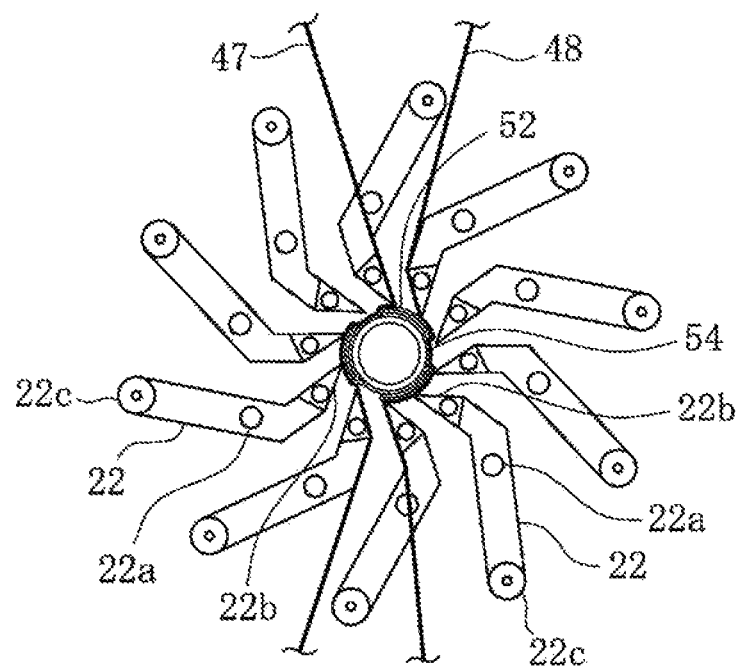
FIG. 15 is a front view of the blades in a state in which the blades are moved rotationally from the state of FIG. 14 to fold the wring shapes of the balloon.

In accordance with an exemplary embodiment, after the balloon 52 formed with the wing shapes is inserted in the folding section 3, the rotary member 23 is rotated by operating the drive source 24, whereon the blades 22 are moved rotationally, the distal portions 22b of the blades 22 come closer to one another, and the central region between the blades 22 is narrowed, as illustrated in FIG. 15. Attendant on this, the balloon 52 inserted in the central region between the blades 22 is put into a state in which the wing shapes are laid flat in the circumferential direction by the distal portions 22b of the blades 22. Since the blades 22 are preliminarily heated before insertion of the balloon 52 and the balloon 52 is heated by the blades 22, the wing shapes laid flat in the circumferential direction by the blades 22 can be maintained in their shape. In accordance with an exemplary embodiment, the blades 22 may be preliminarily cooled.

In this instance, the surfaces of the blades 22 which surfaces make contact with the balloon 52 are covered with the first film 47 and the second film 48, so that the balloon 52 does not make direct contact with the surfaces of the blades 22. After the wing shapes of the balloon 52 are folded, the blades 22 are moved rotationally in the manner of being returned to their original positions. Next, the balloon catheter 50 is detached from the grasping section 110, and the balloon 52 is withdrawn from the folding section 3. Thereafter, the holding of the shaft 51 by the holding portion 32 is released, and wrapping of the balloon 52 of the balloon catheter 50 is completed.

While a case in which the balloon 52 of a rapid exchange type catheter is wrapped by the balloon wrapping apparatus has been described hereinabove, a balloon 52 of an over-the-wire type catheter can also be wrapped by the same balloon wrapping apparatus.

As has been described above, the balloon wrapping apparatus according to the present embodiment is a balloon wrapping apparatus for wrapping a balloon 52 of a balloon catheter 50 provided with the balloon at a distal portion of an elongated shaft 51, and includes: the pleating section 2 that has a plurality of blades 12 (wing forming members) aligned with space parts therebetween in the circumferential direction, and that forms the balloon 52 with wing shapes projecting in radial directions by clamping by the blades 12 the balloon 52 caused to enter into the space parts by moving rotationally the blades 12; the folding section 3 that has a plurality of blades 22 (folding members) aligned in the circumferential direction, and that folds the wing shapes formed in the balloon 52 in the circumferential direction by moving rotationally the blades 22; the support base 4 that supports a part of the shaft 51 which part is on the proximal side of the balloon 52, and that makes the distal portion of the shaft 51 positionable in relation to the pleating section 2 and the folding section 3; and the grasping section 110 capable of grasping a part of the balloon catheter 50 which part is on the distal side of the balloon 52.

In accordance with an exemplary embodiment, the balloon wrapping apparatus configured as above-described has the grasping section 110 for grasping a part of the balloon catheter 50 which part is on the distal side of the balloon 52, and, therefore, the balloon wrapping apparatus can restrain the balloon catheter 50 from bending due to its own weight and can accurately position the balloon 52 in relation to the pleating section 2 and the folding section 3. Accordingly, the wing shapes of the balloon 52 can be formed uniformly in the circumferential direction in the pleating section 2, and occurrence of wrapping in the reverse direction (back folding) in the folding section 3 can be restrained.

In addition, since the support base 4 has the holding portion 32 for maintaining the position of the shaft 51, the support base 4 can clamp the shaft 51 to suitably maintain the position of the shaft 51, and can accurately position the balloon 52 in relation to the pleating section 2 and the folding section 3. In addition, since the shaft 51 can be held by the holding portion 32, a pulling force can be applied to the balloon catheter 50 from the distal side.

In accordance with an exemplary embodiment, since the balloon wrapping apparatus has the pulling section 130 for applying a pulling force to the balloon catheter 50 by moving the grasping section 110 and the holding portion 32 away from each other, it is possible to restrain the balloon catheter 50 from bending due to its own weight, by the pulling force, and to accurately position the balloon 52 in relation to the pleating section 2 and the folding section 3. The pulling force to be applied is preferably, for example, not less than 0.5 N, more preferably 0.5 N to 5 N. In addition, the distance by which the balloon catheter 50 is pulled for applying the pulling force to the balloon catheter 50 is preferably, for example, not less than 1 mm, more preferably 1 mm to 20 mm.

In addition, since the grasping surface of the grasping section 110 is formed of a recessed curved surface, the balloon catheter 50 can be restrained from being damaged when grasped by the grasping section 110, and, owing to a larger contact surface, a high grasping force can be produced.

In addition, since the balloon wrapping apparatus has the core metal member 6 inserted in the shaft 51, a distal portion of the shaft 51 inclusive of the balloon 52 is supported by the core metal member 6 in such a manner as not to bend, and can be accurately positioned, and inserted, in relation to the pleating section 2 and the folding section 3. In accordance with an exemplary embodiment, with the core metal member 6 inserted in the shaft 51, the shaft 51 can be restrained from being crushed at the grasping section 110 or the holding portion 32.

In addition, the present disclosure also includes the balloon wrapping method. The balloon wrapping method is a balloon wrapping method for wrapping a balloon 52 of a balloon catheter 50 provided with the balloon 52 at a distal portion of an elongated shaft 51, the balloon wrapping method including: a step of forming the balloon 52 with wing shapes projecting in radial directions; and a step of folding the wing shapes formed in the balloon 52 along a circumferential direction, in which in at least one of the step of forming the wing shapes and the step of folding the wing shapes along the circumferential direction, a part of the balloon catheter 50 which part is on a distal side of the balloon 52 is grasped and a pulling force is applied to the balloon catheter 50 in a state in which the position of the shaft 51 is maintained.

In the balloon wrapping method configured as above-described, a pulling force is applied to the balloon catheter 50 at the time of forming the balloon 52 with the wing shapes and at the time of folding the wing shapes, and, therefore, bending of the balloon catheter 50 due to its own weight can be restrained from occurring. For this reason, the balloon 52 can be accurately positioned in a position suitable for forming the balloon 52 with the wing shapes or in a position suitable for folding the wing shapes, and the wing shapes of the balloon 52 can be formed uniformly in the circumferential direction or the wing shapes can be folded in an appropriate direction.

In accordance with an exemplary embodiment, the pulling force applied to the balloon catheter 50 can be applied by pulling the balloon catheter with a force, for example, of not less than 0.5 mN. As a result of this, bending of the balloon catheter 50 due to its own weight can be suitably restrained from occurring.

In addition, the pulling force applied to the balloon catheter 50 can be applied by grasping a distal portion of the balloon catheter 50 and then moving the distal portion of the balloon catheter 50, for example, by not less than 1 mm. As a result of this, bending of the balloon catheter 50 due to its own weight can be suitably restrained from occurring.

Note that the present invention is not limited only to the aforementioned embodiment, and various modifications can be made by those skilled in the art within the technical thought of the present invention. For instance, while the two traction sections 100 provided in the pleating section 2 and the folding section 3 are configured in the same structure in the aforementioned embodiment, they may be different in structure. In addition, while the pulling section 130 is provided such as to apply the pulling force to the balloon catheter 50 from the distal side in the aforementioned embodiment, the pulling section may be provided such as to apply the pulling force to the balloon catheter 50 from the proximal side.

Figure 16A:
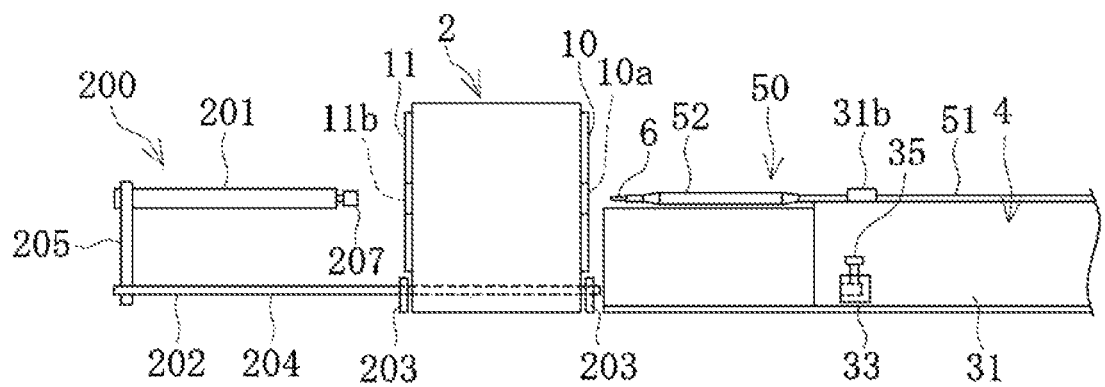
FIGS. 16A-16C are side views of a pleating section according to another embodiment.

Now, a pleating section 2 according to another embodiment will be described below. As illustrated in FIG. 16A, the pleating section 2 according to another embodiment is provided with an insertion assisting section 200 for assisting the insertion of the balloon catheter 50 into the insertion hole 10*a*. The insertion assisting section 200 can be interlocked with the holding base section 31 that holds the shaft 51 of the balloon catheter 50. The insertion assisting section 200 can include an elongated assisting shaft 201, an interlock portion 202 for interlocking the assisting shaft 201 and the holding base section 31, and a support portion 203 for supporting the interlock portion 202 in a slidable manner. The interlock portion 202 can include an elongated interlock shaft 204, and a fixing portion 205 for fixing the assisting shaft 201 and the interlock shaft 204.

In accordance with an exemplary embodiment, one end of the interlock shaft 204 is fixed to the assisting shaft 201 by the fixing portion 205. The other end of the interlock shaft 204 abuts on, and is interlockable with, a holding base side interlock portion 33 of the holding base section 31. The holding base side interlock portion 33 has, for example, a fixing screw 35 for fixing the assisting shaft 201.

The assisting shaft 201 is formed at a distal portion thereof with a cavity portion 207 into which the core metal member 6 to be inserted in the balloon catheter 50 can be inserted. With the core metal member 6 inserted in the cavity portion 207, the balloon catheter 50 can be restrained from bending. Note that the assisting shaft 201 can also hold the shaft 51 of the balloon catheter 50. The assisting shaft 201 can enter a back surface hole 11*b* provided in the pleating section 2 on the side opposite to the insertion hole 10a, and can protrude from the insertion hole 10a to the exterior.

Figure 16B:
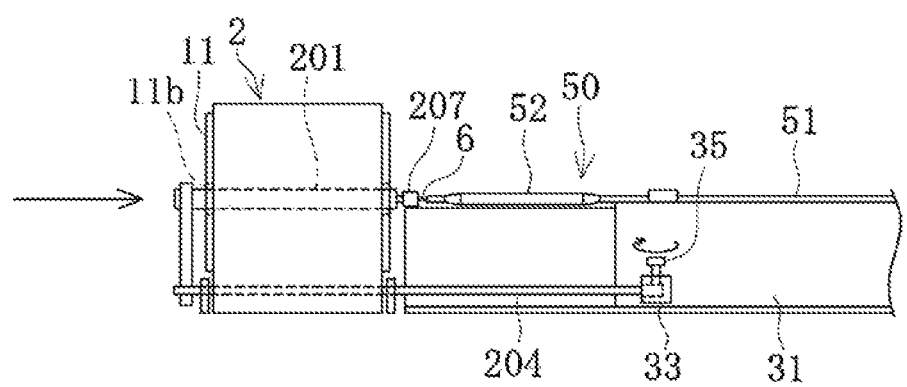
Figure 16C:
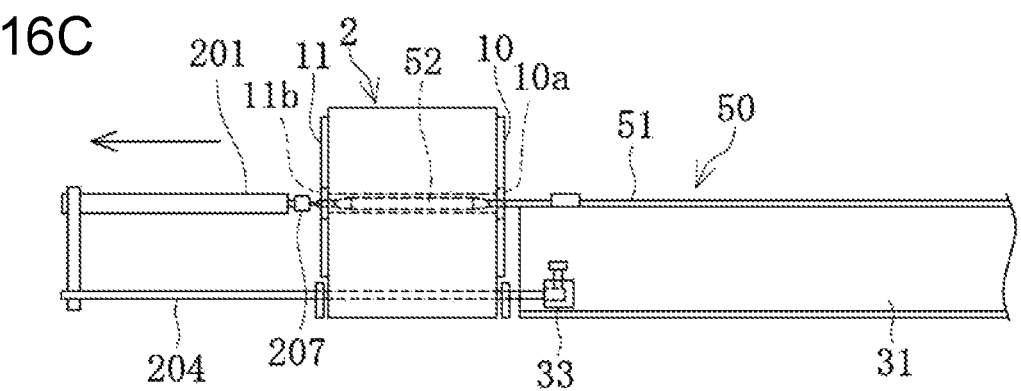

In inserting the balloon catheter 50 into the pleating section 2, the assisting shaft 201 is inserted into the back surface hole 11b of the pleating section 2 and is protruded from the insertion hole 10a, as depicted in FIG. 16B. Next, the core metal member 6 is inserted into the cavity portion 207 of the assisting shaft 201, and the interlock shaft 204 is fixed to the holding base section 31. Thereafter, as depicted in FIG. 16C, the holding base section 31 is moved toward the pleating section 2, whereon the balloon catheter 50 is inserted through the insertion hole 10a into the inside of the pleating section 2. In this instance, the assisting shaft 201 is also moved together with the holding base section 31, and, therefore, the balloon 52 can be inserted into a central area of the blades 12 of the pleating section 2 while a state of the balloon 52 being held by the assisting shaft 201 is maintained. As a result of this, the balloon 52 can be accurately positioned, and inserted, in relation to the pleating section 2. Note that the insertion assisting section 200 may be provided in the folding section 3.

In addition, the support base for holding the balloon catheter 50 may have such a structure as to be able to rotate the balloon catheter 50 about its axis in a state of holding the balloon catheter 50. In this case, with the balloon catheter 50 rotated in a direction reverse to the folding direction, during folding of the wing shapes of the balloon 52 by the folding section 3, the effect of restraining back folding can be further enhanced.

EXAMPLES

Examples of the present invention and Comparative Examples will be described below. Drug-coated balloons of Examples 1 to 4 and Comparative Examples 1 to 9 were produced under the conditions set forth in Tables 1 to 3 (FIGS. 17-19).

Comparative Example 1

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 2.0 mm in diameter and 40 mm in length when inflated, the balloon was inflated at 4 atm, and coating with the coating liquid was slowly conducted such that the amount of paclitaxel on the balloon would be approximately 3.2 µg/mm². After the coating, the balloon catheter was dried, to produce a drug-coated balloon.

(2) Step of Pleating the Drug-Coated Balloon

A core metal member (material: SUS) in the form of wire (solid) 0.39 mm in diameter and 700 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to a holding base section by a holding portion fitted with silicone rubber. In this instance, the three-way cock of the hub of the balloon catheter was attached to an air injection and suction mechanism for inflating and deflating the balloon of the wrapping apparatus. The core metal member protruding from a distal portion of the balloon catheter was inserted into a distal support (assisting shaft) of a pleating section 2. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Comparative Example 2

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 4.0 mm in diameter and 200 mm in length when inflated, the balloon was inflated at 4 atm, and coating with the coating liquid was slowly conducted such that the amount of paclitaxel on the balloon would be approximately 3.6 µg/mm². After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Comparative Example 3

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 3.0 mm in diameter and 200 mm in length when inflated, the balloon was inflated at 4 atm, and coating with the coating liquid was slowly conducted such that the amount of paclitaxel on the balloon would be approximately 3.6 µg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Comparative Example 4

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 2.0 mm in diameter and 200 mm in length when inflated, the balloon was inflated at 4 atm, and coating with the coating liquid was slowly conducted such that the amount of paclitaxel on the balloon would be approximately 3.2 µg/mm$^2$. After the coating, the balloon catheter was dried, to produce a drug-coated balloon.

(2) Step of Pleating the Drug-Coated Balloon

A core metal member (material: SUS) in the form of wire 0.38 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The ten blades were held in a closed state for a while, after which the blades were slowly opened, to spread the first film and the second film. Thereafter, the balloon was drawn back from the folding section.

Comparative Example 5

(1) Production of Drug-Coated Balloon

A coating liquid was prepared by dissolving L-serine ethyl ester hydrochloride (CAS No.: 26348-61-8) and paclitaxel (CAS No.: 33069-62-4) in a mixed liquid of anhydrous ethanol, tetrahydrofuran, acetone and distilled water. A three-way cock was attached to a hub portion of a balloon catheter (material of balloon: nylon, the surface being smooth and non-porous) 6.0 mm in diameter and 200 mm in length when inflated, the balloon was inflated at 4 atm, and coating with the coating liquid was slowly conducted such that the amount of paclitaxel on the balloon would be approximately 3.2 µg/mm$^2$. After the coating, the balloon catheter was dried, to produce a drug-coated balloon.

(2) Step of Pleating the Drug-Coated Balloon

A core metal member (material: SUS) in the form of wire 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. The balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into the distal support (assisting shaft) of the folding section, and the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Example 1

(1) Production of Drug-Coated Balloon

In the same procedure as in the production example of the drug-coated balloon in Comparative Example 1, a drug-coated balloon of a balloon catheter (material of balloon: nylon, the surface being smooth and non-porous) 6.0 mm in diameter and 200 mm in length was produced.

(2) Step of Pleating the Drug-Coated Balloon

A core metal member (material: SUS) in the form of wire 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward by 5 mm and was fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, a collet chuck affixed to a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having eight blades. After the balloon was pushed in completely, the position of the distal support was fixed, and the support base section with the shaft of the balloon catheter fixed thereto was pulled backward by 5 mm and was fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The eight blades were held in a closed state for a while, after which the blades were slowly opened, to spread the first film and the second film, and the balloon was drawn back from the folding section.

Example 2

(1) Production of Drug-Coated Balloon

In the same procedure as in the production example of the drug-coated balloon in Comparative Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward by 5 mm, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward by 5 mm and was then fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first films, and the balloon was drawn back from the folding section.

Example 3

(1) Production of Drug-Coated Balloon

In the same procedure as in the production example of the drug-coated balloon in Comparative Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the distal support was fixed. Subsequently, the support base section with the shaft of the balloon catheter fixed thereto was pulled backward with a force of 5 N, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the distal support was fixed, and the support base section with the shaft of the balloon catheter fixed thereto was pulled backward by a force of 5 N and was fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Example 4

(1) Production of Drug-Coated Balloon

In the same procedure as in the production example of the drug-coated balloon in Comparative Example 1, a drug-coated balloon of a balloon catheter (material of balloon: nylon, the surface being smooth and non-porous) 4.0 mm in diameter and 200 mm in length was produced.

(2) Step of Pleating the Drug-Coated Balloon

A hollow core metal member (material: SUS) 0.48 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into, and fixed to, the collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the position of the support base section with the shaft of the balloon catheter fixed thereto was fixed. Subsequently, the distal support was pulled forward with a force of 1 N, and was then fixed. The heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the films, and the balloon was drawn back from the folding section.

Comparative Example 6

(1) Production of Drug-Coated Balloon

In the same procedure as in the production example of the drug-coated balloon in Comparative Example 1, a drug-coated balloon of a balloon catheter (material of balloon: nylon, the surface being smooth and non-porous) 3.0 mm in diameter and 20 mm in length was produced.

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between a first film and a second film (material: PTFE, thickness: 0.001 mm) which are difficult to electrostatically charge and smooth and which were passed between blades of the pleating section having three blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having twelve blades. After the balloon was pushed in completely, the heated blades were slowly closed, then, from the point of time when the first film and the second film made contact with the wings, the balloon catheter was slowly rotated in the direction reverse to the rotary movement direction of the blades, and the rotation of the balloon was finished before the blades were closed completely. The twelve blades were held in a closed state for a while, after which the blades were slowly opened, to spread the first film and the second film. Thereafter, the balloon was drawn back from the folding section.

Comparative Example 7

(1) Production of Drug-Coated Balloon

In the same procedure as in the production example of the drug-coated balloon in Comparative Example 1, a drug coated balloon of a balloon catheter (material of balloon: nylon, the surface being smooth and non-porous) 4.0 mm in diameter and 200 mm in length was produced. Coating was conducted such that the amount of paclitaxel on the balloon would be approximately 3.6 µg/mm².

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Comparative Example 8

(1) Production of Drug-Coated Balloon

In the same procedure as in the production example of the drug-coated balloon in Comparative Example 1, a drug-coated balloon of a balloon catheter (material of balloon: nylon, the surface being smooth and non-porous) 3.0 mm in diameter and 200 mm in length was produced. Coating was conducted such that the amount of paclitaxel on the balloon would be approximately 3.6 µg/mm².

(2) Step of Pleating the Drug-Coated Balloon

A core metal member (material: SUS) in the form of wire 0.38 mm in diameter and 500 mm in length was inserted into a guide wire lumen of the dried drug-coated balloon, the balloon catheter was placed on a support base of a balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into the distal support (assisting shaft) of the pleating section. Subsequently, the balloon was pushed in between the blades of the pleating section having three blades. Note that the pleating section was not provided with films. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to a folding section. Next, the core metal member protruding from the distal portion of the balloon catheter was inserted into a distal support (assisting shaft) of the folding section, and the balloon portion was pushed in between the blades of the folding section having ten blades. Note that the pleating section was not provided with films. After the balloon was pushed in completely, the heated blades were slowly closed. The ten blades were held in a closed state for a while, after which the blades were slowly opened, and the balloon was drawn back from the folding section.

Comparative Example 9

(1) Production of Drug-Coated Balloon

In the same procedure as in the production example of the drug-coated balloon in Comparative Example 1, a drug-coated balloon of a balloon catheter (material of balloon: nylon, the surface being smooth and non-porous) 2.0 mm in diameter and 200 mm in length was produced.

(2) Step of Pleating the Drug-Coated Balloon

A core metal member (material: SUS) in the form of wire 0.38 mm in diameter and 700 mm in length was inserted into a guide wire lumen of the dried drug-coated balloon, the balloon catheter was placed on the support base of the balloon wrapping apparatus such that the drug coating portion did not make contact with the support base, and a shaft of the balloon catheter was fixed to the holding base section by the holding portion fitted with silicone rubber. In this instance, the three-way cock of the hub of the balloon catheter was attached to the air injection and suction mechanism for inflating and deflating the balloon of the wrapping apparatus. The core metal member protruding from a distal portion of the balloon catheter was inserted into, and fixed to, a collet chuck affixed to the distal support (assisting shaft) of the pleating section. Next, the balloon was pushed in between a first film and a second film (material: PTFE, thickness: 0.001 mm) which are difficult to electrostatically charge and smooth and which were passed between blades of the pleating section having four blades. After the balloon was pushed in completely, the heated blades were slowly closed simultaneously with starting of pleating, to press the blades against the balloon, and air inside the balloon was slowly sucked (removed) to deflate the balloon. The blades were held in the closed state for a while, to form wings, and then the blades were slowly opened, to spread the films. Thereafter, the balloon was drawn back from the pleating section.

(3) Step of Folding the Drug-Coated Balloon

In a condition where the balloon catheter formed with the wings was held in a deflated state, the support base was slid to the folding section. Next, the core metal member protruding from the distal portion of the balloon catheter was inserted into, and fixed to, a collet chuck affixed to the distal support (assisting shaft) of the folding section. Subsequently, the balloon portion was pushed in between a first film and a second film (material: PTFE, thickness: 0.001 mm) which are difficult to electrostatically charge and smooth and which were passed between blades of the folding section having ten blades. After the balloon was pushed in completely, the heated blades were slowly closed. The ten blades were held in a closed state for a while, after which the blades were slowly opened, to spread the first film and the second film. Thereafter, the balloon was drawn back from the folding section.

Measurement of Amount of Paclitaxel Remaining on Balloon After Folding

For the drug-coated balloons produced in Comparative Examples 1 to 5 and Comparative Examples 7 to 9, the amount of paclitaxel remaining on the balloon was measured in the following procedure.

(1) Method

The drug-coated balloon after folding was immersed in a methanol solution, followed by shaking by use of a shaker for 10 minutes, to extract paclitaxel present in the coating on the balloon. The light absorbance, at 227 nm, of the methanol solution into which paclitaxel had been extracted was measured by high-speed liquid chromatography using an ultraviolet-and-visible absorptiometer, and the amount of paclitaxel per balloon ([μg/balloon]) was determined. Further, from the amount of paclitaxel thus obtained and the surface area of the balloon, the amount of paclitaxel per unit area of balloon ([μg/mm$^2$]) was calculated.

(2) Results

In Table 4 (FIG. 20), the amount of paclitaxel (theoretical value) on the balloon upon coating and the amount of paclitaxel (measured value) on the balloon after folding are depicted as amount per unit area. In addition, retention rate of paclitaxel after folding was calculated by dividing the amount of paclitaxel on the balloon after folding by the amount of paclitaxel on the balloon upon coating, and multiplying the quotient by 100.

As depicted in Table 4 (FIG. 20), in every one of Comparative Examples 1 to 5, the retention rate of paclitaxel was high. On the other hand, in Comparative Examples 7 and 8, the retention rate of paclitaxel was as low as less than 80%. Note that the films were used in the pleating and folding in Comparative Examples 1 to 5, but films were not used in the pleating and folding in Comparative Examples 7 and 8. It could be confirmed that detachment of the drug coating layer can be reduced by using films in pleating and folding.

Evaluation of Generation of Back Folding Upon Folding

For the drug-coated balloons prepared under the conditions of Comparative Example 4 and Comparative Example 9, the generation rate of back folding upon folding was evaluated.

(1) Method

The wrapping direction of wings of the drug-coated balloons upon folding was observed on a digital microscope. In the case where the wrapping directions of the wings were not in one direction and there was the wings whose wrapping direction was reverse to the normal direction, the case was counted as back folding.

(2) Results

Table 5 (FIG. 21) depicts the number of drug-coated balloons in which back folding was generated, the total number of drug-coated balloons subjected to folding, and generation rate of back folding. The generation rate of back folding was calculated by dividing the number of drug-coated balloons in which back folding was generated by the total number of drug-coated balloons subjected to folding, and multiplying the quotient by 100.

As depicted in Table 5 (FIG. 21), in the method of Comparative Example 4 in which the balloon was rotated during folding, back folding was scarcely generated. On the other hand, in the method of Comparative Example 9 in which the balloon was not rotated during folding, back folding was generated in approximately one half of the samples subjected to folding. Accordingly, it could be confirmed that the rotation of the balloon during folding has an effect to reduce the generation of back folding.

The detailed description above describes a balloon wrapping apparatus and balloon wrapping method for wrapping a balloon of a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon wrapping apparatus for wrapping a balloon of a balloon catheter provided with the balloon at a distal portion of an elongated shaft, the balloon wrapping apparatus comprising:
   a pleating section having a plurality of wing forming members aligned with spaces between the plurality of wing forming members in a circumferential direction, and configured to form the balloon with wing shapes projecting in radial directions by the wing forming members clamping the balloon, which causes the balloon to enter into the spaces, by moving rotationally the plurality of wing forming members;
   a folding section that has a plurality of folding members aligned in the circumferential direction, and configured to fold the wing shapes formed in the balloon by moving rotationally the plurality of folding members, each of the pleating section and the folding section being disposed on a base;
   a pivotable support base configured to support a part of the elongated shaft which part is on a proximal side of the balloon, the elongated shaft extending in one direction from the balloon, and the support base configured to arrange the distal portion of the elongated shaft positionable in relation to the pleating section and the folding section, the support base having a holding portion configured to maintain a position of the elongated shaft;
   a grasping section provided in the pleating section and in the folding section, the grasping section capable of grasping a part of the balloon catheter which part is on a distal side of the balloon; and
   a pulling section provided in the pleating section and in the folding section, the pulling section configured to apply a pulling force to the balloon catheter by moving the grasping section and the holding portion away from each other, and wherein the pulling section is moved in a distal direction relative to the distal side of the balloon.

2. The balloon wrapping apparatus according to claim 1, wherein the grasping section has a grasping surface formed of a recessed curved surface.

3. The balloon wrapping apparatus according to claim 1, comprising:
   a core metal member that is inserted into the elongated shaft.

4. The balloon wrapping apparatus according to claim 1, wherein each of the plurality of wing forming members is a plate-shaped member, which are disposed at equal angular intervals along the circumferential direction.

5. The balloon wrapping apparatus according to claim 4, wherein the plurality of wing forming members is three in number.

6. The balloon wrapping apparatus according to claim 4, wherein each of the plurality of wing forming members has a rotational center portion on an outer circumferential end portion of the wing forming member and a moving pin extending in an axial direction on an inner circumferential side of the rotational center portion, and wherein each of the moving pins is fitted in a fitting groove formed in a rotary member, which is configured to be rotatable in the pleating section.

7. The balloon wrapping apparatus according to claim 6, wherein when the rotary member is rotated, the moving pins fitted in the fitting grooves are moved in the circumferential direction, whereby each of the plurality of wing shaped member is moved rotationally about the rotational center portion.

8. The balloon wrapping apparatus according to claim 1, wherein each of the plurality of wing forming members is a plate-shaped member, and wherein the plurality of wing forming members are each positioned along an axial direction of the balloon catheter and are disposed such that each of the plurality of plate-shaped member are arranged at equal interval along the circumferential direction.

9. The balloon wrapping apparatus according to claim 8, wherein each of the plurality of wing forming members has a moving pin extending in the axial direction, and wherein each of the moving pins is fitted in a fitting groove formed in a rotary member, which is rotatable in the folding section.

10. The balloon wrapping apparatus according to claim 9, wherein each of the plurality of wing forming members are arranged at an angle of 36° from one another.

11. The balloon wrapping apparatus according to claim 3, wherein the pulling force applied to the balloon catheter is applied by pulling the balloon catheter with a force of not less than 0.5 N.

12. The balloon wrapping apparatus according to claim 11, wherein the pulling force applied to the balloon catheter is applied by grasping a distal portion of the balloon catheter and thereafter moving the distal portion of the balloon catheter by not less than 1 mm.

13. The balloon wrapping apparatus according to claim 1, wherein the pulling section includes a sliding portion configured to fit to a guide groove portion on a base, a pinion configured to mesh with a rack having teeth arranged rectilinearly on the base, and a dial configured to rotate the pinion.

14. The balloon wrapping apparatus according to claim 1, further comprising:
   a first film supplying section configured to supply a film to the plurality of wing forming members in the pleating section, and wherein the film prevents direct contact of a surface of the plurality of wing forming members with the balloon in the pleating section; and
   a second film supplying section configured to supply a film to the plurality of wing forming members in the folding section, and wherein the film prevents direct contact of the surface of the plurality of wing forming members with the balloon in the folding section.

15. A balloon wrapping apparatus for wrapping a balloon of a balloon catheter arranged with the balloon at a distal portion of an elongated shaft, the elongated shaft extending in one direction from the balloon, the balloon wrapping apparatus comprising:
a pleating section having a plurality of blades aligned with spaces between the plurality of blades in a circumferential direction, and configured to form the balloon with wing shapes projecting in radial directions by rotating the blades of the pleating section;
a folding section having a plurality of blades aligned in a circumferential direction, and configured to fold the wing shapes formed in the balloon in the circumferential direction by rotating the blades of the folding section, each of the pleating section and the folding section being disposed on a base and oriented in a different direction by a predetermined angle from each other;
a pivotable support base configured to support a part of an elongated shaft which part is on a proximal side of the balloon, the support base having a holding portion configured to maintain a position of the elongated shaft;
a grasping section provided in the pleating section and in the folding section, the grasping section configured to grasp a part of the balloon catheter, which part is on a distal side of the balloon; and
a pulling section provided in the pleating section and in the folding section, the pulling section configured to apply a pulling force to the balloon catheter by moving the grasping section and the holding portion away from each other, and wherein the pulling section is moved in a distal direction relative to the distal side of the balloon.

16. The balloon wrapping apparatus according to claim 15, wherein each of the plurality of blades of the pleating section are disposed at equal angular intervals along the circumferential direction;
wherein each of the plurality of blades of the pleating section has a rotational center portion on an outer circumferential end portion of the blade of the pleating section and a moving pin extending in an axial direction on an inner circumferential side of the rotational center portion, and wherein each of the moving pins is fitted in a fitting groove formed in a rotary member, which is configured to be rotatable in the pleating section; and
wherein when the rotary member is rotated, the moving pins fitted in the fitting grooves are moved in the circumferential direction, whereby each of the plurality of wing shaped member is moved rotationally about the rotational center portion.

17. The balloon wrapping apparatus according to claim 15, wherein the plurality of blades are each positioned along an axial direction of the balloon catheter and are disposed such that each of the plurality of blades are arranged at equal intervals along the circumferential direction; and
wherein each of the plurality of blades has a moving pin extending in the axial direction, and wherein each of the moving pins is fitted in a fitting groove formed in a rotary member, which is rotatable in the folding section.

18. A balloon wrapping method for wrapping a balloon of a balloon catheter provided with the balloon at a distal portion of an elongated shaft, the balloon wrapping method comprising:
supporting a part of the elongated shaft which part is on a proximal side of the balloon on a support base, the elongated shaft extending in one direction from the balloon, the support base having a holding portion configured to maintain a position of the elongated shaft;
inserting the balloon catheter into a pleating section;
grasping a part of the balloon catheter which part is on a distal side of the balloon with a grasping section in the pleating section;
forming the balloon with wing shapes projecting in radial directions in the pleating section;
pivoting the support base to a folding section;
inserting the balloon catheter into the folding section;
grasping the part of the balloon catheter which part is on the distal side of the balloon with a grasping section in the folding section; and
folding the wing shapes formed in the balloon along a circumferential direction in the folding section, wherein in at least one of the forming the wing shapes and the folding the wing shapes along the circumferential direction, the part of the balloon catheter which part is on the distal side of the balloon is grasped and a pulling force is applied to the balloon catheter in a state in which the position of the elongated shaft is maintained with a pulling section configured to move the grasping section and the holding portion away from each other and by moving the pulling section in a distal direction relative to the distal side of the balloon.

19. The balloon wrapping method according to claim 18, wherein the pulling force applied to the balloon catheter is applied by pulling the balloon catheter with a force of not less than 0.5 N.

20. The balloon wrapping method according to claim 18, wherein the pulling force applied to the balloon catheter is applied by grasping a distal portion of the balloon catheter and thereafter moving the distal portion of the balloon catheter by not less than 1 mm.

* * * * *